(12) United States Patent
Kallenbach et al.

(10) Patent No.: US 7,902,327 B2
(45) Date of Patent: Mar. 8, 2011

(54) DENDRIMERIC PEPTIDES, PHARMACEUTICAL COMPOSITIONS AND METHODS OF USING THE SAME

(75) Inventors: Neville Robert Kallenbach, Philadelphia, PA (US); Anne W. Young, Brooklyn, NY (US); Zhigang Liu, New York, NY (US); Chunhui Zhou, Woodhaven, NY (US)

(73) Assignee: New York University School of Medicine, New York, NY (US)

( * ) Notice: Subject to any disclaimer, the term of this patent is extended or adjusted under 35 U.S.C. 154(b) by 0 days.

(21) Appl. No.: 12/154,659

(22) Filed: May 22, 2008

(65) Prior Publication Data

US 2008/0312159 A1 Dec. 18, 2008

Related U.S. Application Data

(60) Provisional application No. 60/931,317, filed on May 22, 2007.

(51) Int. Cl.
*A61K 38/05* (2006.01)
*A61K 31/04* (2006.01)
*C07K 5/06* (2006.01)
(52) U.S. Cl. ...................................... 530/323; 514/21.91
(58) Field of Classification Search ........................ None
See application file for complete search history.

(56) References Cited

U.S. PATENT DOCUMENTS

| | | | |
|---|---|---|---|
| 5,428,016 A | 6/1995 | Tomita et al. | |
| 6,313,095 B1 | 11/2001 | Adams et al. | |
| 6,835,536 B2 | 12/2004 | Krieger et al. | |
| 7,026,282 B1 | 4/2006 | Plough et al. | |
| 2006/0240510 A1 | 10/2006 | Valtanen et al. | |
| 2007/0053934 A1 * | 3/2007 | Kallenbach et al. | 424/204.1 |

OTHER PUBLICATIONS

Bacterial infection versus viral infection from http://www.mayoclinic.com/health/infectious-disease/AN00652, pp. 1-4. Accessed Jul. 6, 2009.*
Fungal infection from Merck manual, http://www.merck.com/mmhe/sec17/ch197/ch197a.html, pp. 1-3. Accessed Jul. 6, 2009.*
Definition of Stereoisomers from www.chemicool.com/definition/steroisomers.html, pp. 1-3. Accessed Jul. 22, 2009.*
Definition of tautomer from http://medical-dictionary.thefreedictionary.com/tautomer, pp. 1-2. Accessed Jul. 22, 2009.*
Definition of isomers from www.answers.com/topic/isomer, pp. 1-10. Accessed Jul. 29, 2009.*
Hensley Scott, "Zyrtec Looks in Mirror and Sees Xyzal," from http://blogs.wsj.com/health/2007/05/29/zyrtec-looks-in-mirror-and-sees-xyzal/, pp. 1-3. Accesssed Jul. 29, 2009.*
More Daniel, "Xyzal: Stateof the Art Antihistamine," from http://allergies.about.com/b/2007/10/09/xyzal-state-of-the-art-antihistamine.htm, p. 1. Accessed Jul. 29, 2009.*
Thalidomide D or L safe from http://www/skingenious.com/faq.html, pp. 1-7. Accessed Jul. 29, 2009.*

* cited by examiner

*Primary Examiner* — Julie Ha
(74) *Attorney, Agent, or Firm* — Klauber & Jackson LLC

(57) ABSTRACT

Novel dendrimeric peptide compounds are disclosed that have a formula represented by the following formula I:

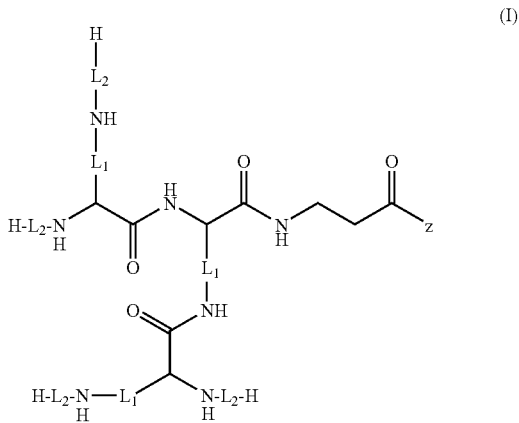

The compounds demonstrate antimicrobial activity and may be prepared as pharmaceutical compositions and used for the prevention and treatment of a variety of conditions in mammals including humans where microbial invasion is involved. The present peptides are particularly valuable as their effect is rapid, broad in spectrum and mostly indifferent to resistance provoked by standard antibiotics.

17 Claims, 11 Drawing Sheets

Blank control

25 μg/mL Hexamer

50 μg/mL Hexamer

25 μg/mL Dendrimer

50 μg/mL Dendrimer

Killing curves by $(RW)_4D$ were evaluated at a peptide concentration of $5 \times MIC_{50}$ MRSA with 10 μ M of Vancomycin MRSA with 10 μ M of (RW)4D A. baumannii with 10 μ M of Vancomycin A. baumannii with 10 μ M of (RW)4D Live/DEAD staining assay of cells after 1 hr of incubation. Green stained cells are alive, red are not.

5 min 300 min

Confocal laser scanning microscopy study. *E. coli* cells treated with 40 nM rhodamine-labeled (RW)$_{4D}$ after different time of incubation.

Fig. 14A        Fig. 14B
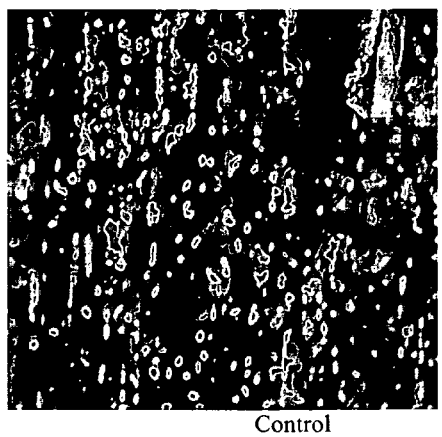  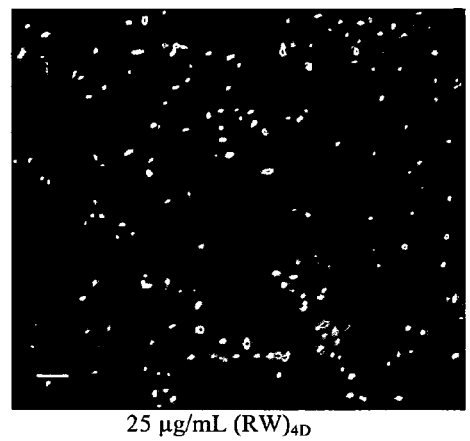
Control        25 μg/mL (RW)$_{4D}$
Fig. 15A        Fig. 15B
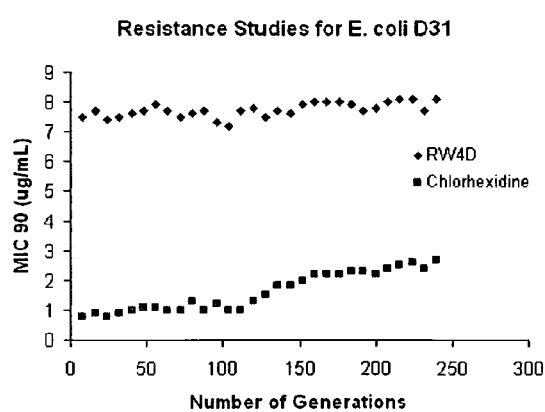  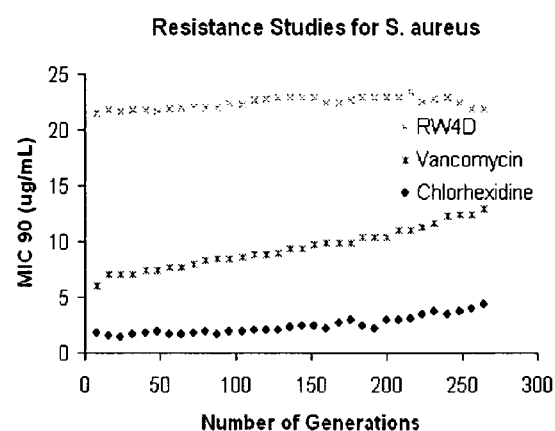

US 7,902,327 B2

DENDRIMERIC PEPTIDES, PHARMACEUTICAL COMPOSITIONS AND METHODS OF USING THE SAME

RELATED APPLICATION

The present application claims the benefit under 35 U.S.C. §119 of U.S. Provisional Application Ser. No. 60/931,317 filed May 22, 2007, the contents of which application is hereby incorporated by reference in its entirety.

GOVERNMENT SUPPORT

This invention was made at least in part, with government support under Grant No. N00014-03-1-0129 awarded by the Office of Naval Research. Accordingly, the United States Government has certain rights in the invention.

FIELD OF THE INVENTION

This invention relates to novel compositions containing active peptides, and particularly, such peptides as demonstrate antimicrobial, antifungal or antiviral activity. The invention also relates to methods for the preparation of the peptide compositions, and their use in preventing and/or treating conditions resulting from the unwanted presence of microbial, fungal or viral activity.

BACKGROUND OF THE INVENTION

For the last few decades it has been known that a wide range of antimicrobial peptides are secreted by all manner of multicellular organisms in response to infection by foreign viruses, bacteria or fungi. Current research focuses on the mechanism by which the peptides kill, and synthetic design strategies which can enhance the activity of the peptides to a useful therapeutic level.

A wide range of antimicrobial peptides is secreted in plants and animals to challenge attack by foreign viruses, bacteria or fungi (Boman, 2003). These form part of the innate immune in response to infection, which is short term and fast acting relative to humoral immunity (Medzhitov, 2000). These cationic antimicrobial peptides have been considered as prospective antibiotics agents because their effect is rapid, broad spectrum and indifferent to resistance to standard antibiotics such as penicillins (Fischetti, 2003; Hancock, 1999). However, their success thus far has been limited, and is believed to be due to the requirement that they be present in a fairly high concentration to achieve killing (Hancock, 2000, PNAS), which is believed to exert a potentially cytotoxic effect on human erythrocytes as well as other cells and tissues. For these reasons current applications of these peptides are mostly topical.

Hundreds of such antimicrobial peptides have been studied extensively in order to understand the relationship between the structural features of the peptides and their antimicrobial activity, for the purpose of designing a new generation of antibiotics. Such known antimicrobial peptides are listed at (http://aps.unmc.edu/AP/database/antiV.php) and the content and disclosure of this site is incorporated herein by reference in its entirety. Representative peptides listed at the site are set forth hereinbelow by way of illustration and not limitation. Known antimicrobial peptides differ strikingly in size, sequence and structure, sharing only amphipathicity and positive charge (Hancock, 1999; Zasloff, 2002). While the external cell wall may be the initial target, several lines of evidence suggest that antimicrobial peptides act by lysing bacterial membranes. Cells become permeable following exposure to peptides, and their membrane potential is correspondingly reduced. While the actual target and mode of action of antimicrobial peptides are incompletely understood, proposed models emphasize the need to coat or cover a significant part of the membrane in order to produce a lethal effect. In "barrel-stave" models, several peptide monomers need to bind before formation of an aggregate that inserts itself into the bilayer to form a transmembrane pore. (Ehrenstein, 1977). In a somewhat different view, known as the "carpet model," peptide monomers must coat the target membrane surface extensively before sections of the membrane split off as vesicles, thereby destroying the integrity of the membrane (Shai, 2001). Both mechanisms account for the observed threshold concentration required for peptides to achieve lethality differently. In many cases this threshold is close to that for inflicting damage on host cells or tissues, as detected by hemolysis assays for example. Thus peptides have not found wide applications except as topical agents.

Several strategies have been pursued in efforts to increase the effectiveness of antimicrobial peptides (Tam, 2002; Janiszewska, 2003; Tam, 2000; Dathe, 2004; Tang, 1999; Dempsey, 2003; Epand, 2004; Papo, 2004). Sequence changes in natural peptides can notably reduce hemolysis while preserving activity (Staubitz). Inserting unnatural D-amino acids or beta-amino acids into peptide sequences, combinatorial designs based on linear or cyclic sequences (Houghton, Ghadiri), synthetic chemical mimetics (DeGrado, Tew), and multivalent dendrimeric constructs of short peptides (Janiszewska, 2003; Xing, 2003) are other alternatives. In some cases improved solubility, salt resistance, stability and toxicity have been reported, with some reduction in $IC_{50}$ (Tam, 2002).

Accordingly, many different designs for therapeutics have been reported, seeking to develop or improve activity under physiological conditions, low toxicity and proteolytic stability. Among promising approaches, polyvalent or multivalent antimicrobial polymers offers promise for enhancing the efficacy of existing antimicrobial monomer peptide and minimizing the problems accompanying conventional antimicrobial peptides by reducing the toxicity of the residue, increasing their efficiency and selectivity, and prolonging the lifetime of the effect. Especially, these include their ability to amplify cationic charges and hydrophobic clusters as the number of monomer increases. (Tam, 2002). For example, the multivalency of peptides incorporated with fragments of known antibacterial peptides in dendrimers has appeared to demonstrate good activity in the design of membranolytic peptides for therapeutic applications (Tam, 2002).

In this connection, U.S. Pat. No. 5,229,490 to Tam discloses a particular polymeric construction formed by the binding of multiple antigens to a dendritic core or backbone, the objective of which is to potentiate the concentration of antigen within a more economical and efficient molecule. While this construction has demonstrated advantages, greater activity and corresponding stability of the construct is still an important objective that is not fulfilled therein.

U.S. Pat. No. 3,679,653 to Schuck et al. discloses the preparation and use of polymer-based protein complexes, and particularly, relates to the preparation of such complexes with hormones such as bovine growth hormone, insulin and the like. Schuck et al. however, prepare complexes with full length native hormones, and bind the native material to the polymer backbone for the purpose of improving the delivery and availability of such hormones. The inventors qualify that the level of activity of the resulting complexes are somewhat uncertain, and in any event, do not represent that any dramatic improvements in such activity are either anticipated or realized.

Antimicrobial peptides (AMPs) have been proposed as prospective antibiotic agents because of their ability to rapidly inactivate a wide range of microorganisms including Gram-positive and negative bacteria, fungi and some viruses. In many cases they are indifferent to current multi-drug resistant strains (Hancock and Chapple 1999; Lehrer and Ganz 1999).

From the above, it remains that a continuing need exists for the development of modalities that can deliver effective antibiotic peptides in a manner that confers both improved stability and economy of the therapeutic, but importantly, significantly improves the therapeutic efficacy and strength of the resultant molecule. It is toward the fulfillment of these and other related objectives that the present invention is directed.

SUMMARY OF THE INVENTION

It has now been found that antibiotic peptide molecules covalently bound thereto, may be prepared, that provides enhanced stability, such as resistance to enzymatic digestion, along with dramatically increased activity of the antibiotic active. In this latter regard, increases in activity on the order of ten-fold or more, over the same peptides in conventional form, are attained. This finding leads to novel peptides having therapeutic value. It also leads to pharmaceutical compositions having the peptide of the present invention as an active ingredient and to their use to treat, prevent or ameliorate a range of conditions in mammals of various genesis or etiology, however, primarily caused by bacteria, viruses, or fungi.

More particularly, the present invention relates to peptides having antimicrobial properties, according to formula I:

wherein
each $L^1$ is $-(CH_2)_n-$; n is 2, 3, 4 or 5; each $L^2$ is a dipeptide or a tripeptide linker; and Z is selected from substituted or unsubstituted amino, hydroxy, substituted or unsubstituted alkoxy, and substituted or unsubstituted aryloxy; or a pharmaceutically acceptable salt, solvate or prodrug thereof; and stereoisomers, isotopic variants and tautomers thereof.

In one embodiment, with respect to peptides of formula I, each $L^1$ is selected from $-CH_2-CH_2-$, $-CH_2-CH_2-CH_2-$, and $-CH_2-CH_2-CH_2-CH_2-$. In a preferred embodiment, each $L^1$ is $-CH_2-CH_2-CH_2-CH_2-$.

In one embodiment, with respect to peptides of formula I, each $L^2$ is selected from RWW, RFF, RYY, KWW, KYY and KFF.

In another embodiment, with respect to peptides of formula I, each $L^2$ is selected from WWR, FFR, YYR, WWK, YYK and FFK.

In one embodiment, with respect to peptides of formula I, each $L^2$ is selected from RW, RW*, RF, RY, R-2Nal, H*W, KW, KY and KF.

In another embodiment, with respect to peptides of formula I, each $L^2$ is selected from WR, W*R, FR, YR, 2Nal-R, WH*, WK, YK and FK.

In yet another embodiment, with respect to peptides of formula I, each $L^2$ is WR.

In yet another embodiment, with respect to peptides of formula I, each $L^2$ is W*R.

In yet another embodiment, with respect to peptides of formula I, each $L^2$ is FR.

In yet another embodiment, with respect to peptides of formula I, each $L^2$ is YR.

In yet another embodiment, with respect to peptides of formula I, each $L^2$ is 2Nal-R.

In yet another embodiment, with respect to peptides of formula I, each $L^2$ is WH*.

In yet another embodiment, with respect to peptides of formula I, each $L^2$ is WK.

In yet another embodiment, with respect to peptides of formula I, each $L^2$ is YK.

In yet another embodiment, with respect to peptides of formula I, each $L^2$ is FK.

In a preferred embodiment, with respect to peptides of formula I, each $L^2$ is WR.

In another embodiment, with respect to peptides of formula I, each $L^2$ is as described in the preceding paragraphs; and R, W, W*, F, Y, H*, K, and 2-Nal are as defined herein.

In one embodiment, with respect to peptides of formula I, each Z is selected from $NH_2$, substituted or unsubstituted alkylamino, substituted or unsubstituted arylamino, substituted or unsubstituted alkoxy, and substituted or unsubstituted aryloxy.

In another embodiment, with respect to peptides of formula I, each Z is selected from $NH_2$, alkyl amino, arylamino, alkoxy and aryloxy.

In another embodiment, with respect to peptides of formula I, each Z is selected from $NH_2$, nonylamino, benzylamino, and benzyloxy.

In a particular embodiment, with respect to peptides of formula I, Z is $NH_2$.

In a particular embodiment, with respect to peptides of formula I, Z is nonylamino.

In a particular embodiment, with respect to peptides of formula I, Z is benzylamino.

In a particular embodiment, with respect to peptides of formula I, Z is benzyloxy.

In a particular embodiment, with respect to peptides of formula I, Z is OH.

In a further aspect, the present invention provides a method for the preparation of the peptides of the invention.

In a further aspect, the peptides of the invention may be used to treat microbial or fungal conditions affecting lower animals, and possibly, plants. The peptides could be designed and assembled to include the peptides pertinent for the treatment of a particular microbe or fungus of interest, and then formulated into appropriate compositions and dosage forms for administration or application to an affected host. Moreover, such compositions may comprise the peptides of the invention in mixtures or combinations with other antibiotic agents, such as known antibiotic compounds. In such formulations, the peptides of the invention coact synergistically with the known antibiotic compounds, so that the resulting composition demonstrates improved effectiveness.

In a further aspect, the present invention provides pharmaceutical compositions comprising a peptide of the invention, and a pharmaceutical carrier, excipient or diluent. In this aspect of the invention, the pharmaceutical composition can comprise one or more variant peptides of the invention, prepared, for example, with a differing array of peptide linkers, to afford a more comprehensive treatment in the instance where a multiplicity of microbial/viral/fungal antigens are known to be present. Likewise, and as stated above, the pharmaceutical compositions may comprise one or more of the peptides of the invention, in combination with other antibiotic agents or compounds, including known antibiotic compounds.

In a further aspect of the invention, a method is disclosed for treating mammals, including humans, as well as lower mammalian species, susceptible to or afflicted with a condition attributable to or resulting from amicrobial, viral or fungal infection, which method comprises administering an effective amount of a pharmaceutical composition containing or comprising the peptides just described.

In additional aspects, this invention provides methods for synthesizing the complexes of the invention, with representative synthetic protocols and pathways disclosed later on herein.

Other objects and advantages will become apparent to those skilled in the art from a consideration of the ensuing detailed description, which proceeds with reference to the following illustrative drawings.

BRIEF DESCRIPTION OF THE DRAWINGS

(FIGS. 1C and 1D) enzyme incubation time-dependent effect on the antibacterial activity of AMPs; the trypsin concentration is 1 µM. The concentration of AMPs in the experiments is their $MIC_{50}$.

FIG. 2 depicts the results with dendrimer $(RW)_{4D}$. Buffer alone was used as the positive control and $H_2O_2$ was used as the negative control. The results are the mean of three independent experiments performed in parallel.

FIGS. 14A and 14B comprises two plates of photomicrographs presenting a visualization of the results of Live/Dead staining demonstrating the inhibition of E. coli biofilm formation.

FIGS. 15A and 15B graphically demonstrate the effectiveness of dendrimers of the invention in the inhibition of biofilm formation by E. coli and S. aureus.

DETAILED DESCRIPTION OF THE INVENTION

Definitions

Figure 1:
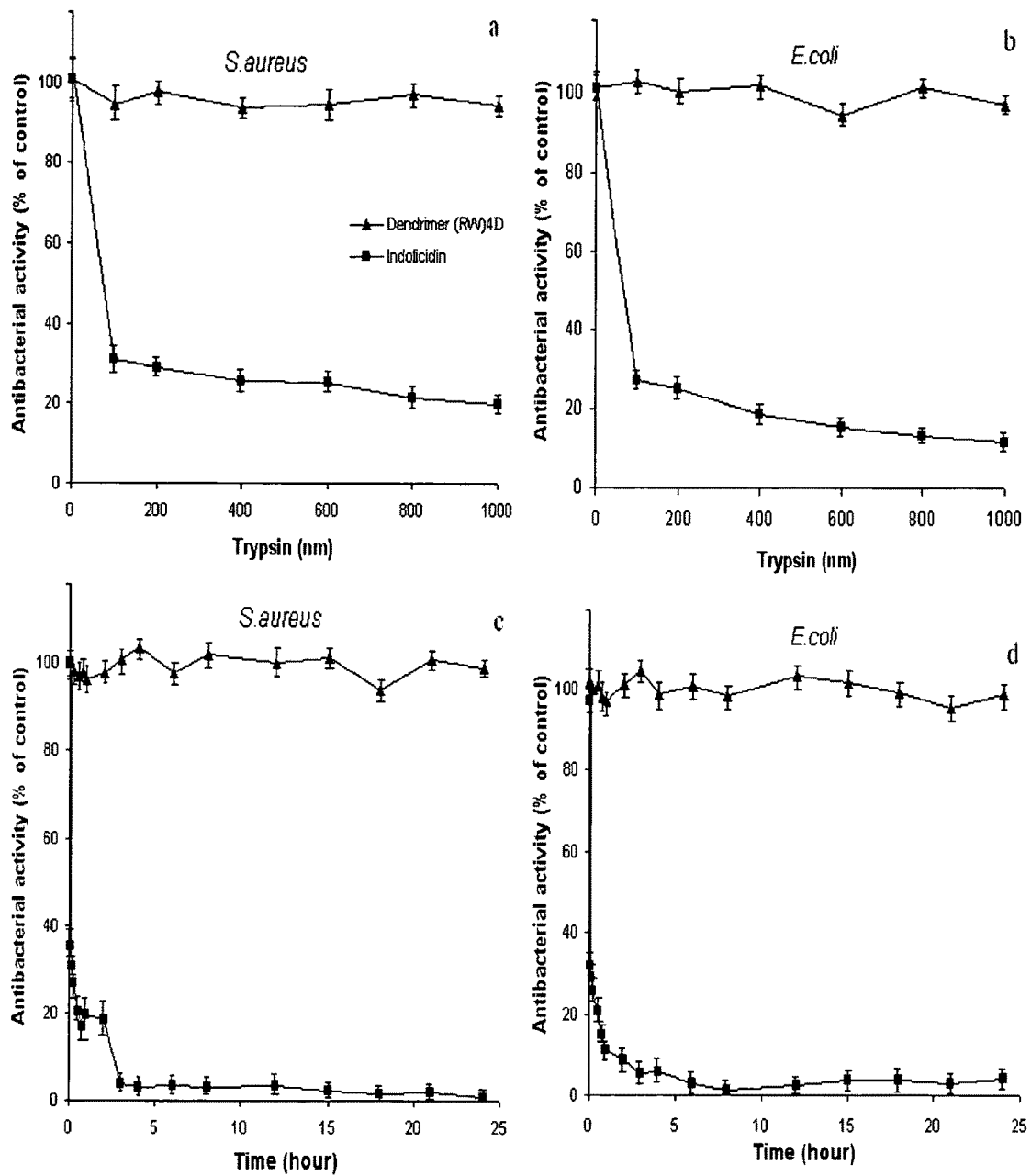
FIGS. 1A-1D are graphs illustrating the protease stability of AMPs (FIGS. 1A and 1B), and the enzyme concentration-dependent effect on the antibacterial activity of AMPs after 1 hr incubation.

When describing the compounds, pharmaceutical compositions containing such compounds and methods of using such compounds and compositions, the following terms have the following meanings herein, unless otherwise indicated.

"Trp (W)" refers herein to an L-Tryptophan residue.
"Phe (F)" refers herein to an L-Phenylalanine residue.
"Lys (K)" refers herein to an L-Lysine residue.
"Arg (R)" refers herein to an L-Arginine residue.
"Tyr (Y)" refers herein to an L-Tyrosine residue.
"His (H*)" refers herein to a Histidine residue.
"(2Nal)" refers herein to 2-naphthyl)-L-alanine, and has a structure according to the following formula, when depicted as a residue:

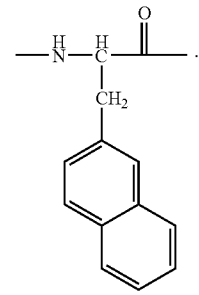

"(W*)" means 5-fluoro-DL-tryptophan, and has a structure according to the following formula, when depicted as a residue:

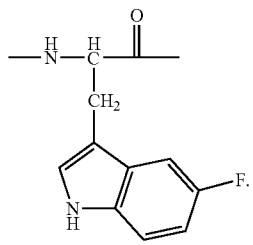

"Peptide" means a chain of amino acid residues having between 2 and about 100 amino acid residues, and includes peptides which are purified from naturally occurring products, or produced by synthetic or recombinant DNA methods, or that include one or more 'unnatural amino acids' as defined herein. Amino acid chains having greater than about 100 amino acid residues if present herein, are referred to as polypeptides.

The term "residue" as used herein, refers to the monomeric form of an amino acid as it exists in a polymeric molecule. In this form, a hydrogen atom is displaced from the N-terminal end, and a hydroxyl group is displaced from the C-terminal end.

"Unnatural amino acids" means amino acids and corresponding peptides that are synthesized from single amino acid starting materials. Such unnatural amino acids may be prepared and used individually in accordance with the present invention, or may incorporated into existing proteins. This method may be used to create analogs with unnatural amino acids. A general method for site-specific incorporation of unnatural amino acids into proteins is described in Christopher J. Noren, Spencer J. Anthony-Cahill, Michael C. Griffith, Peter G. Schultz, *Science*, 244:182-188 (April 1989).

'Alkyl' means straight or branched aliphatic hydrocarbon having 1 to about 20 carbon atoms. Particular alkyl has 1 to about 12 carbon atoms. More particular is lower alkyl which has 1 to 6 carbon atoms. Most particular are groups such as methyl, ethyl and propyl. Branched means that one or more lower alkyl groups such as methyl, ethyl or propyl is attached to a linear alkyl chain. The term $C_1$-$C_6$ alkyl includes both branched and straight chain groups, exemplary straight chain groups include ethyl, propyl, butyl, exemplary branched chain groups include isopropyl, isoamyl, and the like.

'Aryl' refers to a monovalent aromatic hydrocarbon group derived by the removal of one hydrogen atom from a single carbon atom of a parent aromatic ring system. In particular aryl refers to an aromatic ring structure, mono-cyclic or polycyclic that includes from 5 to 12 ring members, more usually 5 to 10. Where the aryl group is a monocyclic ring system it preferentially contains 6 carbon atoms. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene and trinaphthalene. Particularly aryl groups include phenyl, naphthyl, indenyl, and tetrahydronaphthyl.

'Alkoxy' refers to the group —$OR^{24}$ where $R^{24}$ is alkyl. Particular alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

'Substituted alkoxy' includes those groups recited in the definition of 'substituted' herein, and particularly refers to an alkoxy group having 1 or more substituents, for instance from 1 to 5 substituents, and particularly from 1 to 3 substituents, selected from the group consisting of acyl, acylamino, acyloxy, alkoxy, substituted alkoxy, alkoxycarbonyl, alkoxycarbonylamino, amino, substituted amino, aminocarbonyl, aminocarbonylamino, aminocarbonyloxy, aryl, aryloxy, azido, carboxyl, cyano, cycloalkyl, substituted cycloalkyl, halogen, heteroaryl, hydroxyl, keto, nitro, thioalkoxy, substituted thioalkoxy, thioaryloxy, thioketo, thiol, alkyl-S(O)—, aryl-S(O)—, alkyl-S(O)$_2$— and aryl-S(O)$_2$—.

'Aryloxy' refers to —O-aryl groups wherein 'aryl' is as defined above.

'Amino' refers to the radical —$NH_2$.

'Arylamino' means a radical —$NHR^{40}$ where $R^{40}$ represents an aryl group as defined herein.

'Substituted amino' refers to an amino group substituted with one or more of those groups recited in the definition of 'substituted' herein, and particularly refers to the group —$N(R^{36})_2$ where each $R^{36}$ is independently selected from the group consisting of hydrogen, alkyl, substituted alkyl, alkenyl, substituted alkenyl, alkynyl, substituted alkynyl, aryl, cycloalkyl, substituted cycloalkyl, and where both R groups are joined to form an alkylene group. When both R groups are hydrogen, —$N(R^{36})_2$ is an amino group. Exemplary 'substituted amino' groups are —$NR^{36}$—$C_1$-$C_8$ alkyl, —$NR^{36}$—$(CH_2)_t(C_6$-$C_{10}$ aryl), —$NR^{36}$—$(CH_2)_t(C_5$-$C_{10}$ heteroaryl), —$NR^{36}$—$(CH_2)_t(C_3$-$C_{10}$ cycloalkyl), and —$NR^{36}$—$(CH_2)_t(C_5$-$C_{10}$ heterocycloalkyl), wherein t is an integer from 0 to 4, each $R^{36}$ independently represents H or $C_1$-$C_6$ alkyl and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy.

'Substituted' refers to a group in which one or more hydrogen atoms are each independently replaced with the same or different substituent(s). Typical substituents are selected from the group consisting of: —X, —$R^{46}$, —$O^-$, =O, —$OR^{46}$, —$SR^{46}$, —$S^-$, =S, —$NR^{46}R$=$NR^{46}$, —$CX_3$, —$CF_3$, —CN, —OCN, —SCN, —NO, —$NO_2$, =$N_2$, —$N_3$, —$S(O)_2O^-$, —$S(O)_2OH$, —$S(O)_2R^{46}$, —$OS(O_2)O^-$, —OS$(O)_2R^{46}$, —$P(O)(O^-)_2$, P(O)(O$R^{46}$)(O$^-$), —OP(O)(O$R^{46}$)(O$R^{47}$), —C(O)$R^{46}$, C(S)$R^{46}$, —C(O)O$R^{46}$, —C(O)N$R^{46}R^{47}$, —C(O)O$^-$, —C(S)O$R^{46}$, —NR C(O)N$R^{46}R^{47}$, —N$R^{48}$C(S)N$R^{46}R^{47}$, —N$R^{49}$C(N$R^{48}$)N$R^{46}R^{47}$ and —C(N$R^{48}$)N$R^{46}R^{47}$, where each X is independently a halogen; each $R^{46}$, $R^{47}$, $R^{48}$ and $R^{49}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl, substituted heteroarylalkyl, —$NR^{50}R^{51}$, —C(O)$R^{50}$ or —S(O)$_2R^{50}$ or optionally $R^{50}$ and $R^{51}$ together with the atom to which they are both attached form a cycloheteroalkyl or substituted cycloheteroalkyl ring; and $R^{50}$ and $R^{51}$ are independently hydrogen, alkyl, substituted alkyl, aryl, substituted alkyl, arylalkyl, substituted alkyl, cycloalkyl, substituted alkyl, cycloheteroalkyl, substituted cycloheteroalkyl, heteroalkyl, substituted heteroalkyl, heteroaryl, substituted heteroaryl, heteroarylalkyl or substituted heteroarylalkyl. In a particular embodiment, substituted groups are substituted with one or more substituents, particularly with 1 to 3 substituents, in particular with one substituent group. In a further particular embodiment the substituent group or groups are selected from halo, cyano, nitro, trifluoromethyl, trifluoromethoxy, azido, —NR'''SO$_2$R'', —SO$_2$NR''R''', —C(O)R'', —C(O)OR'', —OC(O)R'', —NR C(O)R'', —C(O)NR''R''', —NR''R''', —(CR'''R''')$_m$OR''', wherein, each R'' is independently selected from H, $C_1$-$C_8$ alkyl, —(CH$_2$)$_t$(C$_6$-C$_{10}$ aryl), —(CH$_2$)$_t$(C$_5$-C$_{10}$ heteroaryl), —(CH$_2$)$_t$(C$_3$-C$_{10}$ cycloalkyl), and —(CH$_2$)$_t$(C$_5$-C$_{10}$ heterocycloalkyl), wherein t is an integer from 0 to 4 and any aryl, heteroaryl, cycloalkyl or heterocycloalkyl groups present, may themselves be substituted by $C_1$-$C_4$ alkyl, halo, $C_1$-$C_4$ alkoxy, $C_{1-4}$ haloalkyl, $C_1$-$C_4$ hydroxyalkyl, or $C_1$-$C_4$ haloalkoxy or hydroxy. Each R'' independently represents H or $C_1$-$C_6$alkyl.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable vehicle" refers to a diluent, adjuvant, excipient or carrier with which a compound of the invention is administered.

'Preventing' or 'prevention' refers to a reduction in risk of acquiring or developing a disease or disorder (i.e., causing at least one of the clinical symptoms of the disease not to develop in a subject that may be exposed to a disease-causing agent, or predisposed to the disease in advance of disease onset.

"Prodrugs" refers to compounds, including derivatives of the compounds provided herein, which have cleavable groups and become by solvolysis or under physiological conditions the compounds provided herein which are pharmaceutically active in vivo. Such examples include, but are not limited to, choline ester derivatives and the like, N-alkylmorpholine esters and the like.

The term 'prophylaxis' is related to 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

"Solvate" refers to forms of the compound that are associated with a solvent, usually by a solvolysis reaction. Conventional solvents include water, ethanol, acetic acid and the like. The compounds provided herein may be prepared e.g. in crystalline form and may be solvated or hydrated. Suitable solvates include pharmaceutically acceptable solvates, such as hydrates, and further include both stoichiometric solvates and non-stoichiometric solvates.

"Subject" includes humans. The terms "human," "patient" and "subject" are used interchangeably herein.

"Tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the aci- and nitro-forms of phenylnitromethane, that are likewise formed by treatment with acid or base.

Tautomeric forms may be relevant to the attainment of the optimal chemical reactivity and biological activity of a compound of interest.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

'Treating' or 'treatment' of any disease or disorder refers, in one embodiment, to ameliorating the disease or disorder (i.e., arresting the disease or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or disorder, either physically, (e.g., stabilization of a discernible symptom), physiologically, (e.g., stabilization of a physical parameter), or both.

Other derivatives of the compounds provided herein have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well know to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds provided herein are preferred prodrugs. In some cases it is desirable to prepare double ester type prodrugs such as (acyloxy)alkyl esters or ((alkoxycarbonyl)oxy)alkylesters. Preferred are the $C_1$ to $C_8$ alkyl, $C_2$-$C_8$ alkenyl, aryl, $C_7$-$C_{12}$ substituted aryl, and $C_7$-$C_{12}$ arylalkyl esters of the compounds provided herein.

As used herein, the term "isotopic variant" refers to a compound that comprises an unnatural proportion of an isotope of one or more of the atoms that constitute such compound. For example, an "isotopic variant" of a compound can comprise an unnatural proportion of one or more non-radioactive isotopes, such as for example, deuterium ($^2$H or D), carbon-13 ($^{13}$C), nitrogen-15 ($^{15}$N), or the like. It will be understood that, in a compound comprising an unnatural proportion of an isotope, any example of an atom where present, may vary in isotope composition. For example, any hydrogen may be $^2$H/D, or any carbon may be $^{13}$C, or any nitrogen may be $^{15}$N, and that the presence and placement of such atoms may be determined within the skill of the art. Likewise, provided herein are methods for preparation of isotopic variants with radioisotopes, in the instance for example, where the resulting compounds may be used for drug and/or substrate tissue distribution studies. The radioactive isotopes tritium, i.e. $^3$H, and carbon-14, i.e. $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy. All isotopic variants of the compounds provided herein, radioactive or not, are intended to be encompassed within the scope provided herein.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The Peptides

As set forth earlier herein, the peptide dendrimer compounds comprise antimicrobial/antiviral/antifungal peptides. The compounds may be dipeptides and may have a lethal effect on bacteria, viruses or fungi. More particularly, the peptides may be any antimicrobial peptides, including natural products found in organisms, fragments of natural peptides, and any synthetic analogs or de novo designs. These peptides can accordingly include nonnatural amino acids: beta-amino acids, d-amino acids and/or non-indigenous amino acids.

More particularly, the present invention relates to peptides having antimicrobial properties, according to formula I:

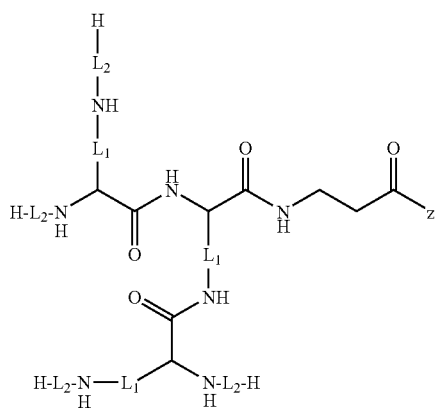

wherein
each $L^1$ is —$(CH_2)_n$—; n is 2, 3, 4 or 5; each $L^2$ is a dipeptide or tripeptide linker; and Z is selected from substituted or unsubstituted amino, hydroxy, substituted or unsubstituted alkoxy, and substituted or unsubstituted aryloxy; or a pharmaceutically acceptable salt, solvate or prodrug thereof; and stereoisomers, isotopic variants and tautomers thereof.

In one embodiment, with respect to peptides of formula I, each $L^1$ is selected from —$CH_2$—$CH_2$—, —$CH_2$—$CH_2$—$CH_2$—, and —$CH_2$—$CH_2$—$CH_2$—$CH_2$—. In a preferred embodiment, each $L^1$ is —$CH_2$—$CH_2$—$CH_2$—$CH_2$—.

In one embodiment, with respect to peptides of formula I, each $L^2$ is selected from RWW, RFF, RYY, KWW, KYY and KFF.

In another embodiment, with respect to peptides of formula I, each $L^2$ is selected from WWR, FFR, YYR, WWK, YYK and FFK.

In one embodiment, with respect to peptides of formula I, each $L^2$ is selected from RW, RW*, RF, RY, R-2Nal, H*W, KW, KY and KF.

In another embodiment, with respect to peptides of formula I, each $L^2$ is selected from WR, W*R, FR, YR, 2Nal-R, WH*, WK, YK and FK.

In yet another embodiment, with respect to peptides of formula I, each $L^2$ is WR.

In yet another embodiment, with respect to peptides of formula I, each $L^2$ is W*R.

In yet another embodiment, with respect to peptides of formula I, each $L^2$ is FR.

In yet another embodiment, with respect to peptides of formula I, each $L^2$ is YR.

In yet another embodiment, with respect to peptides of formula I, each $L^2$ is 2Nal-R.

In yet another embodiment, with respect to peptides of formula I, each $L^2$ is WH*.

In yet another embodiment, with respect to peptides of formula I, each $L^2$ is WK.

In yet another embodiment, with respect to peptides of formula I, each $L^2$ is YK.

In yet another embodiment, with respect to peptides of formula I, each $L^2$ is FK.

In a preferred embodiment, with respect to peptides of formula I, each $L^2$ is WR.

In another embodiment, with respect to peptides of formula I, each $L^2$ is as described in the preceding paragraphs; and R, W, W*, F, Y, H*, K, and 2-Nal are as defined herein.

In one embodiment, with respect to peptides of formula I, each Z is selected from $NH_2$, substituted or unsubstituted alkylamino, substituted or unsubstituted arylamino, substituted or unsubstituted alkoxy, and substituted or unsubstituted aryloxy.

In another embodiment, with respect to peptides of formula I, each Z is selected from $NH_2$, alkylamino, arylamino, alkoxy and aryloxy.

In another embodiment, with respect to peptides of formula I, each Z is selected from $NH_2$, nonylamino, benzylamino, and benzyloxy.

In a particular embodiment, with respect to peptides of formula I, Z is $NH_2$.

In a particular embodiment, with respect to peptides of formula I, Z is nonylamino.

In a particular embodiment, with respect to peptides of formula I, Z is benzylamino.

In a particular embodiment, with respect to peptides of formula I, Z is benzyloxy.

In another embodiment, with respect to peptides of formula I, each Z is OH.

In one embodiment, with respect to peptides of formula I, the peptide is according to formula II:

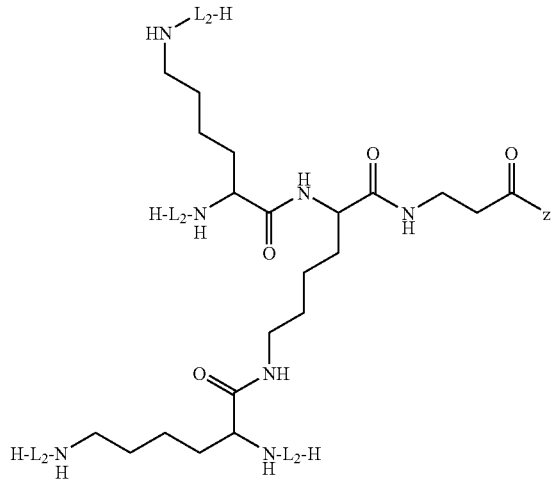

(II)

and wherein each L² and Z is as described with formula I.

In one embodiment, with respect to peptides of formula II, each L² is selected from RWW, RFF, RYY, KWW, KYY and KFF.

In another embodiment, with respect to peptides of formula II, each L² is selected from WWR, FFR, YYR, WWK, YYK and FFK.

In one embodiment, with respect to peptides of formula II, each L² is selected from RW, RW*, RF, RY, R-2Nal, H*W, KW, KY and KF.

In another embodiment, with respect to peptides of formula II, each L² is selected from WR, W*R, FR, YR, 2Nal-R, WH*, WK, YK and FK.

In yet another embodiment, with respect to peptides of formula II, each L² is WR.

In yet another embodiment, with respect to peptides of formula II, each L² is W*R.

In yet another embodiment, with respect to peptides of formula II, each L² is FR.

In yet another embodiment, with respect to peptides of formula II, each L² is YR.

In yet another embodiment, with respect to peptides of formula II, each L² is 2Nal-R.

In yet another embodiment, with respect to peptides of formula II, each L² is WH*.

In yet another embodiment, with respect to peptides of formula II, each L² is WK.

In yet another embodiment, with respect to peptides of formula II, each L² is YK.

In yet another embodiment, with respect to peptides of formula II, each L² is FK.

In a preferred embodiment with respect to peptides of formula II, each L² is WR.

In one embodiment, with respect to peptides of formula II, each Z is selected from NH₂, substituted or unsubstituted alkylamino, substituted or unsubstituted arylamino, substituted or unsubstituted alkoxy, and substituted or unsubstituted aryloxy.

In another embodiment, with respect to peptides of formula II, each Z is selected from NH₂, alkylamino, arylamino, alkoxy and aryloxy.

In another embodiment, with respect to peptides of formula II, each Z is selected from NH₂, nonylamino, benzylamino, and benzyloxy.

In a particular embodiment, with respect to peptides of formula II, Z is NH₂.

In a particular embodiment, with respect to peptides of formula II, Z is nonylamino.

In a particular embodiment, with respect to peptides of formula II, Z is benzyl amino.

In a particular embodiment, with respect to peptides of formula II, Z is benzyloxy.

In a particular embodiment, with respect to peptides of formula II, Z is hydroxy.

In one embodiment, with respect to peptides of formula I, the peptide is according to formula III:

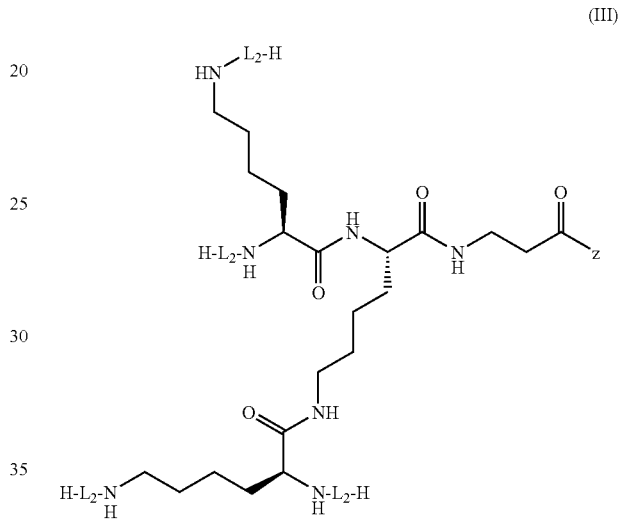

(III)

and wherein each L² and Z is as described with formula I.

In one embodiment, with respect to peptides of formula III, each L² is selected from RWW, RFF, RYY, KWW, KYY and KFF.

In another embodiment, with respect to peptides of formula III, each L² is selected from WWR, FFR, YYR, WWK, YYK and FFK.

In one embodiment, with respect to peptides of formula III, each L² is selected from RW, RW*, RF, RY, R-2Nal, H*W, KW, KY and KF.

In another embodiment, with respect to peptides of formula III, each L² is selected from WR, W*R, FR, YR, 2Nal-R, WH*, WK, YK and FK.

In yet another embodiment, with respect to peptides of formula III, each L² is WR.

In yet another embodiment, with respect to peptides of formula III, each L² is W*R.

In yet another embodiment, with respect to peptides of formula III, each L² is FR.

In yet another embodiment, with respect to peptides of formula III, each L² is YR.

In yet another embodiment, with respect to peptides of formula III, each L² is 2Nal-R.

In yet another embodiment, with respect to peptides of formula III, each L² is WH*.

In yet another embodiment, with respect to peptides of formula III, each L² is WK.

In yet another embodiment, with respect to peptides of formula III, each L² is YK.

In yet another embodiment, with respect to peptides of formula III, each $L^2$ is FK.

In a preferred embodiment with respect to peptides of formula III, each $L^2$ is WR.

In one embodiment, with respect to peptides of formula III, each Z is selected from $NH_2$, substituted or unsubstituted alkylamino, substituted or unsubstituted arylamino, substituted or unsubstituted alkoxy, and substituted or unsubstituted aryloxy.

In another embodiment, with respect to peptides of formula III, each Z is selected from $NH_2$, alkylamino, arylamino, alkoxy and aryloxy.

In another embodiment, with respect to peptides of formula III, each Z is selected from $NH_2$, nonylamino, benzylamino, and benzyloxy.

In a particular embodiment, with respect to peptides of formula III, Z is $NH_2$.

In a particular embodiment, with respect to peptides of formula III, Z is nonylamino.

In a particular embodiment, with respect to peptides of formula III, Z is benzylamino.

In a particular embodiment, with respect to peptides of formula III, Z is benzyloxy.

In one embodiment, with respect to peptides of formula I, the peptide is according to formula IV:

(IV)

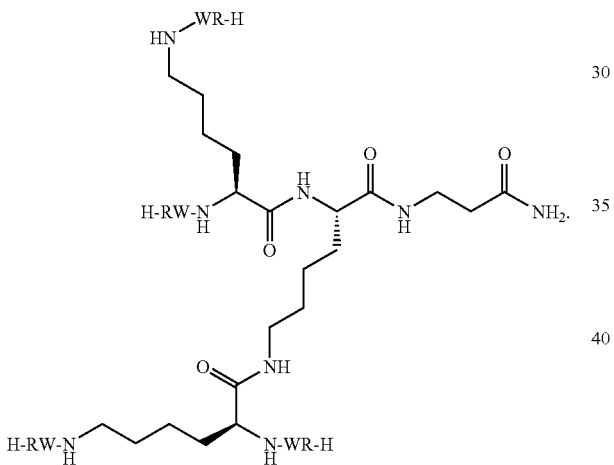

In one embodiment, with respect to peptides of formula I, the peptide is according to formula V:

(V)

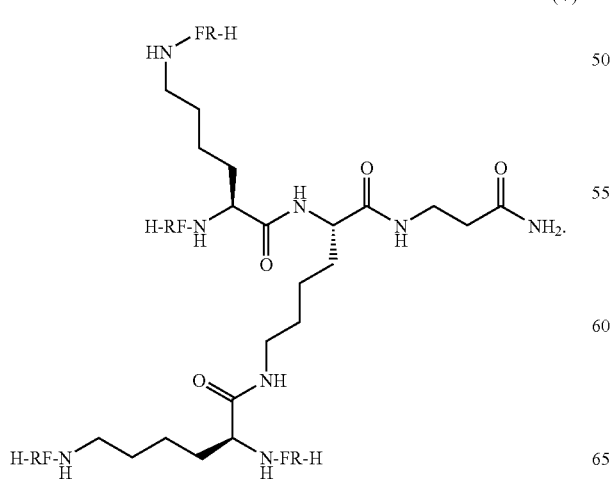

In one embodiment, with respect to peptides of formula I, the peptide is according to formula VI:

(VI)

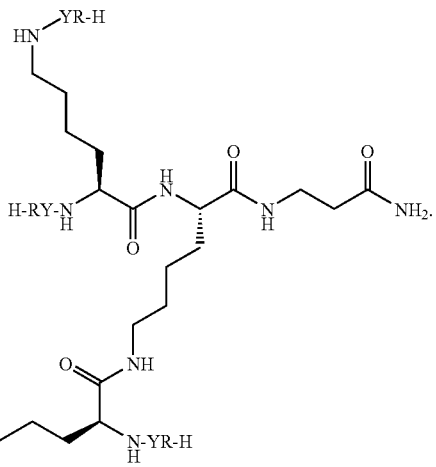

In one embodiment, with respect to peptides of formula I, the peptide is according to formula VII:

(VII)

In one embodiment, with respect to peptides of formula I, the peptide is according to formula VIII:

(VIII)

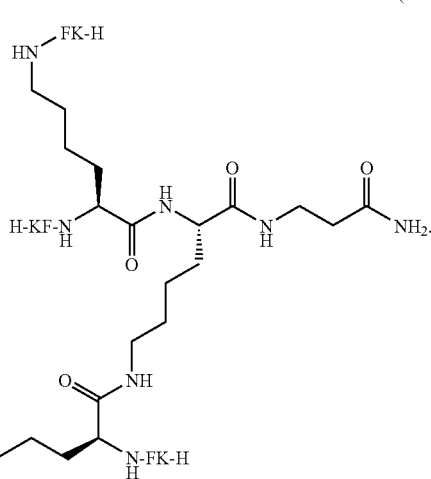

In one embodiment, with respect to peptides of formula I, the peptide is according to formula IX:

(IX)

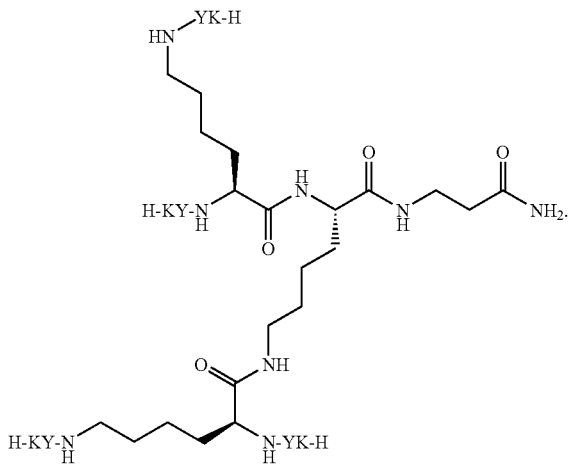

In one embodiment, with respect to peptides of formula I, the peptide is according to formula X:

(X)

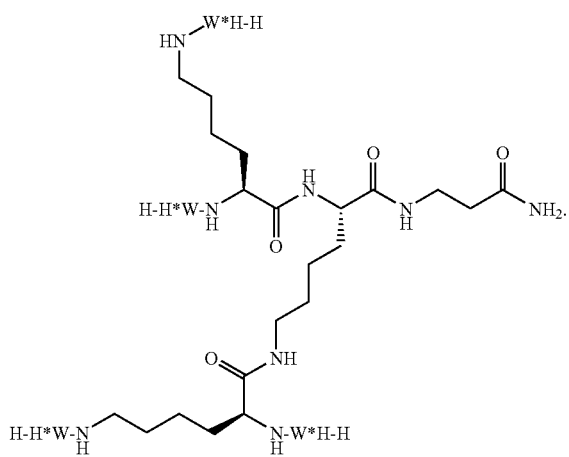

In one embodiment, with respect to peptides of formula I, the peptide is according to formula XI:

(XI)

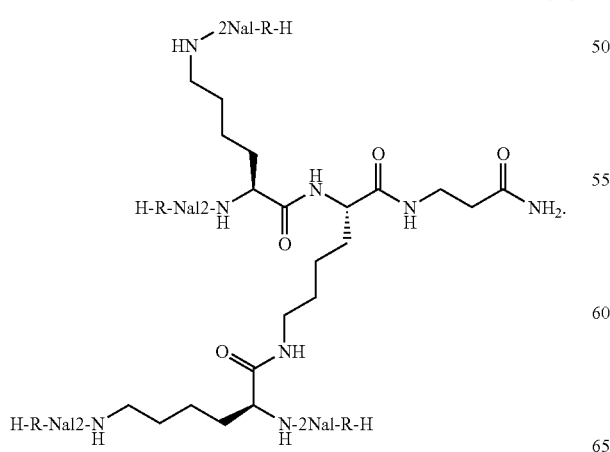

In one embodiment, with respect to peptides of formula I, the peptide is according to formula XII:

(XII)

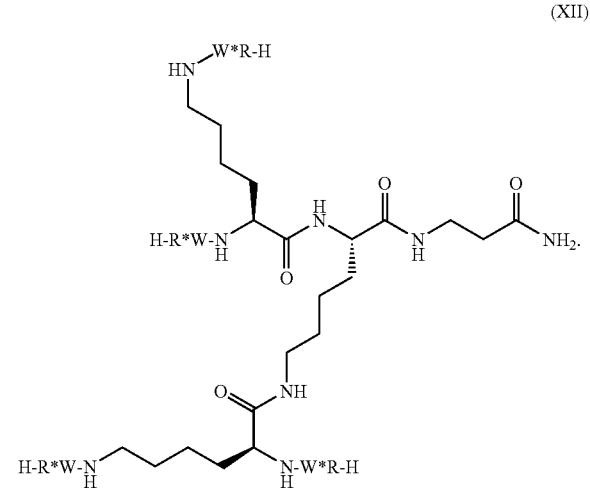

In one embodiment, with respect to peptides of formula I, the peptide is according to formula XIII:

(XIII)

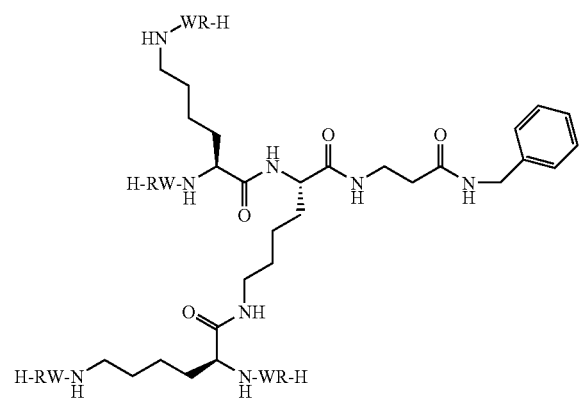

In one embodiment, with respect to peptides of formula I, the peptide is according to formula XIV:

(XIV)

In one embodiment, with respect to peptides of formula I, the peptide is according to formula XV:

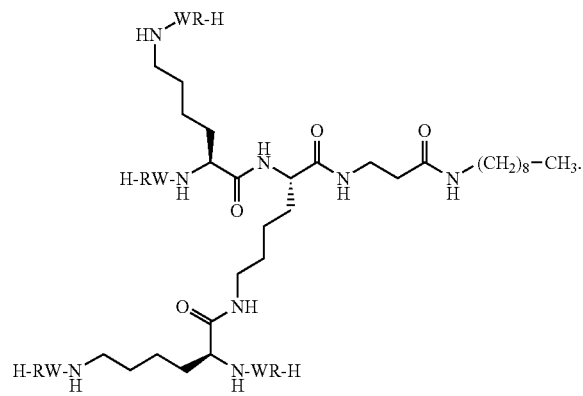

In certain aspects and where appropriate, the present invention extends to the preparation of prodrugs and derivatives of the peptides of the invention. Prodrugs are derivatives which have cleavable groups and become by solvolysis or under physiological conditions the peptide of the invention, which are pharmaceutically active, in vivo.

Pharmaceutical Compositions

When employed as pharmaceuticals, the peptide compounds of this invention are typically administered in the form of a pharmaceutical composition. Such compositions can be prepared in a manner well known in the pharmaceutical art and comprise at least one active complex. In a further embodiment, the pharmaceutical compositions of the invention may comprise one or more of the peptide compounds in combination with one or more non-peptide antibiotic compounds, including known antibiotic compounds. Such combinations yield compositions that exhibit improved effectiveness over like compositions containing the active compounds individually, so that a synergistic effect of the combination is conferred. The exact amounts and proportions of the compounds with respect to each other may vary within the skill of the art.

Generally, the peptide compound of this invention is administered in a pharmaceutically effective amount. The amount of the complex actually administered will typically be determined by a physician, in the light of the relevant circumstances, including the condition to be treated, the chosen route of administration, the actual complex administered, the age, weight, and response of the individual patient, the severity of the patient's symptoms, and the like.

The pharmaceutical compositions of this invention can be administered by a variety of routes including by way of non limiting example, oral, rectal, transdermal, subcutaneous, intravenous, intramuscular and intranasal. Depending upon the intended route of delivery, the compounds of this invention are preferably formulated as either injectable or oral compositions or as salves, as lotions or as patches all for transdermal administration.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the furansulfonic acid compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the active compound in such compositions is typically a minor component, often being from about 0.05 to 10% by weight with the remainder being the injectable carrier and the like.

Transdermal compositions are typically formulated as a topical ointment or cream containing the active ingredient(s), generally in an amount ranging from about 0.01 to about 20% by weight, preferably from about 0.1 to about 20% by weight, preferably from about 0.1 to about 10% by weight, and more preferably from about 0.5 to about 15% by weight. When formulated as an ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or the formulation. All such known transdermal formulations and ingredients are included within the scope of this invention.

The compounds of this invention can also be administered by a transdermal device. Accordingly, transdermal administration can be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of *Remington's Pharmaceutical Sciences,* 17th edition, 1985, Mack Publishing Company, Easton, Pa., which is incorporated herein by reference.

The compounds of this invention can also be administered in sustained release forms or from sustained release drug delivery systems. A description of representative sustained release materials can be found in *Remington's Pharmaceutical Sciences.*

The following formulation examples illustrate representative pharmaceutical compositions that may be prepared in accordance with this invention. The present invention, however, is not limited to the following pharmaceutical compositions.

Formulation 1

Tablets

A compound of the invention is admixed as a dry powder with a dry gelatin binder in an approximate 1:2 weight ratio. A minor amount of magnesium stearate is added as a lubricant. The mixture is formed into 240-270 mg tablets (80-90 mg of active compound per tablet) in a tablet press.

Formulation 2

Capsules

A compound of the invention is admixed as a dry powder with a starch diluent in an approximate 1:1 weight ratio. The mixture is filled into 250 mg capsules (125 mg of active compound per capsule).

Formulation 3

Liquid

A compound of the invention (125 mg) may be admixed with sucrose (1.75 g) and xanthan gum (4 mg) and the resultant mixture may be blended, passed through a No. 10 mesh U.S. sieve, and then mixed with a previously made solution of microcrystalline cellulose and sodium carboxymethyl cellulose (11:89, 50 mg) in water. Sodium benzoate (10 mg), flavor, and color are diluted with water and added with stirring. Sufficient water may then added to produce a total volume of 5 mL.

Formulation 4

Tablets

A compound of the invention may be admixed as a dry powder with a dry gelatin binder in an approximate 1:2 weight ratio. A minor amount of magnesium stearate is added as a lubricant. The mixture is formed into 450-900 mg tablets (150-300 mg of active compound) in a tablet press.

Formulation 5

Injection

A compound of the invention is dissolved or suspended in a buffered sterile saline injectable aqueous medium to a concentration of approximately 5 mg/mL.

Formulation 6

Topical

Stearyl alcohol (250 g) and a white petrolatum (250 g) are melted at about 75° C. and then a mixture of a compound of the invention (50 g) methylparaben (0.25 g), propylparaben (0.15 g), sodium lauryl sulfate (10 g), and propylene glycol (120 g) dissolved in water (about 370 g) is added and the resulting mixture is stirred until it congeals.

Methods of Treatment

The present complexes may be used as therapeutic agents for the treatment of conditions in mammals. Accordingly, the complexes and pharmaceutical compositions of this invention find use as therapeutics for preventing and/or treating infections and like maladies resulting from bacterial, viral or fungal attack, and related conditions in mammals including humans.

In a method of treatment aspect, this invention provides a method of treating a mammal susceptible to or afflicted with a condition associated with or resulting from bacterial, viral or fungal attack or infection, which method comprises administering an effective amount of one or more of the pharmaceutical compositions just described.

In additional method of treatment aspects, this invention provides methods of treating a mammal susceptible to or afflicted with a variety of bacteria or other infections, including strains which have developed resistance to traditional antibiotics, such as, for example, *Staphylococcus aureus*. The method comprises administering an effective condition-treating or condition-preventing amount of one or more of the pharmaceutical compositions just described.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

For the prevention and/or treatment of long-term conditions, such as viral or microbial conditions, the regimen for treatment usually stretches over many months or years so oral dosing is preferred for patient convenience and tolerance. With oral dosing, one to five and especially two to four and typically three oral doses per day are representative regimens. Using these dosing patterns, each dose provides from about 0.01 to about 20 mg/kg of the compound or its derivative, with preferred doses each providing from about 0.1 to about 10 mg/kg and especially about 1 to about 5 mg/kg.

Transdermal doses are generally selected to provide similar or lower blood levels than are achieved using injection doses.

The complexes of this invention can be administered as the sole active agent or they can be administered in combination with other agents, including other active derivatives.

General Synthetic Procedures

The complexes of this invention can be prepared from readily available starting materials using the general methods and procedures described earlier and illustrated schematically in the examples that follow. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The following methods are presented with details as to the preparation of representative peptides that have been listed hereinabove. The peptides of the invention may be prepared from known or commercially available starting materials and reagents by one skilled in the art of organic synthesis.

Representative Synthetic Method

Preparation of Dendrimeric Peptides of the Invention

The dendrimeric antimicrobial peptides in accordance with a first embodiment of the invention can be prepared using the representative synthetic pathway depicted in Scheme 1. Representative dendrimers are Compounds I-9, presented after the following scheme and the description of the synthetic method.

First, an Fmoc-protected β-alanine residue, making up the C-terminus, was coupled to Rink amide resin. This residue was deprotected and coupled to Fmoc-Lys(Fmoc)-OH with Fmoc-protected α- and ε-amino groups. Using the same protecting group for both amino groups allows for simultaneous deprotection, so that two amide bonds are formed during the next coupling step. Tetravalent cores were achieved by repeating this step. In effect, 4 free amino groups were created respectively.

Then 4 dipeptides ($L^2$) were simultaneously coupled to $NH_2$ groups of the lysine core template. Crude peptide solutions were deprotected by 95% TFA, 2.5% water, 2.5% TIS, precipitated in ether and purified on reverse phase HPLC.

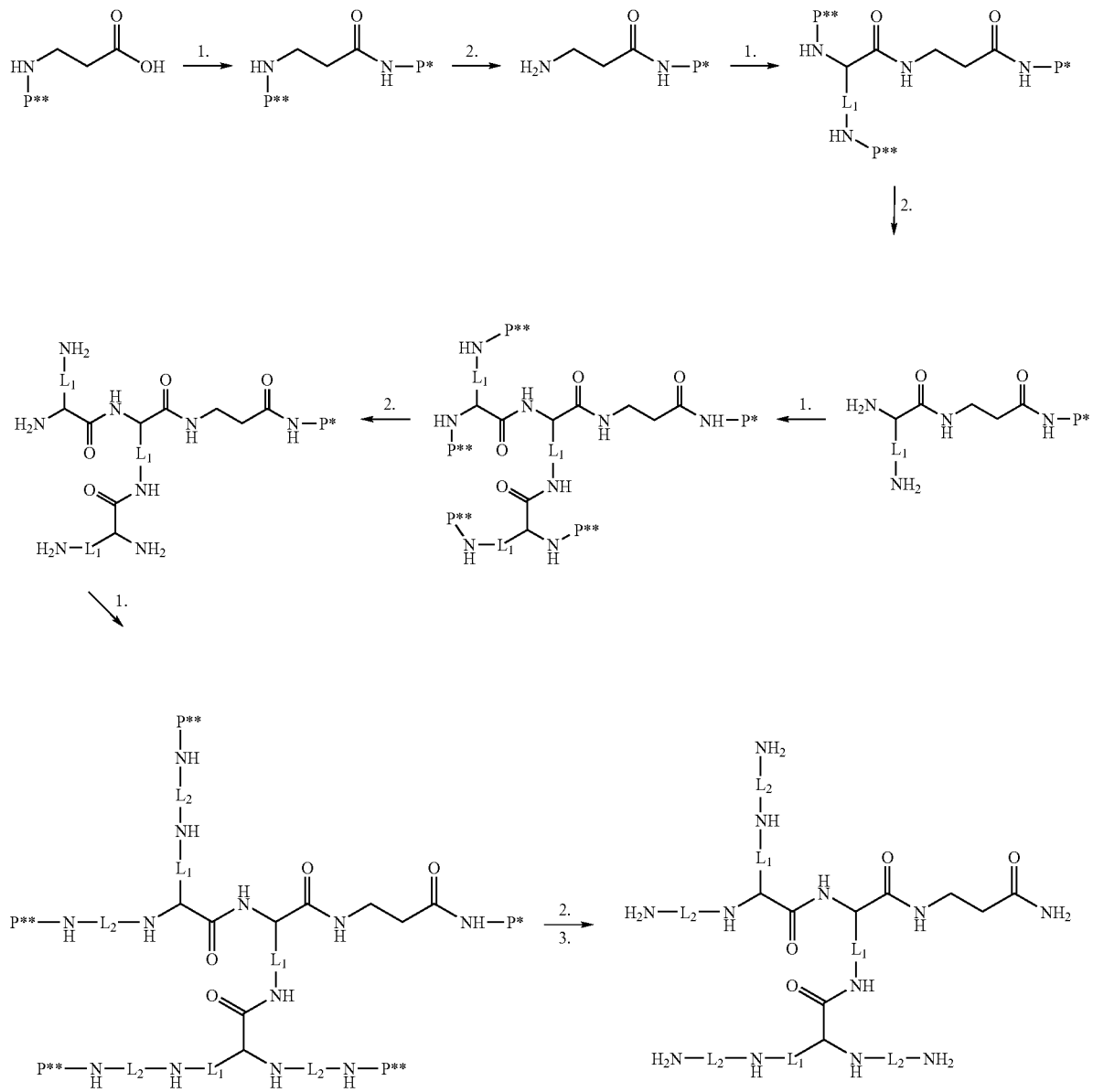

P*-Rink amide resin
P**-Fmoc
1. HOBt/HBTU/DIEA
2. Piperidine
3. 95% TFA/2.5% TIS/2.5% $H_2O$ Molecular weights were verified by M/S using a Bruker MALDI-TOF spectrometer, which were in agreement with theoretical masses.

The following representative amino acids are used for $L^2$ dipeptide linkers:

Trp (W)
Phe (F)
Lys (K)
Arg (R) and
Try (Y).

The following representative $L^2$ dipeptide linkers are used to prepare peptides of the invention.

RW
RW*
RF
RY
R-2Nal
H*W
KW
KY and
KF.

The following representative $L^2$ tripeptide linkers can be used to prepare peptides of the invention.

RWW
RFF
RYY
KWW
KYY and
KFF.

Compound 2 [Den(RF)$_{4D}$]

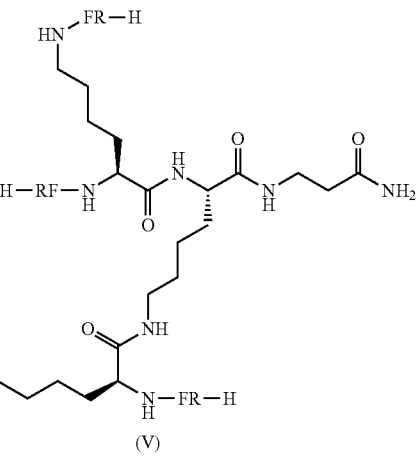

(V)

M + H$^+$ calcd 1686.0, found 1686.5.

Compound 3 [Den(RY)$_{4D}$]

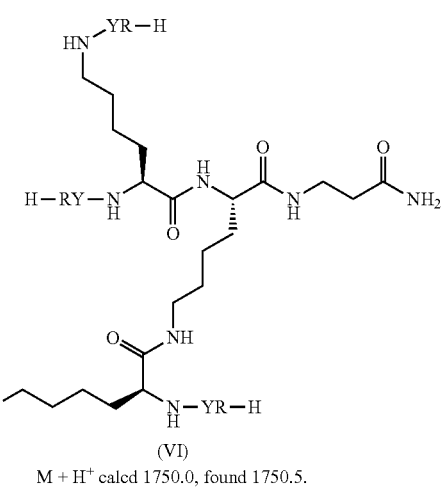

(VI)

M + H$^+$ calcd 1750.0, found 1750.5.

Compound 1 [Den(RW)$_{4D}$]

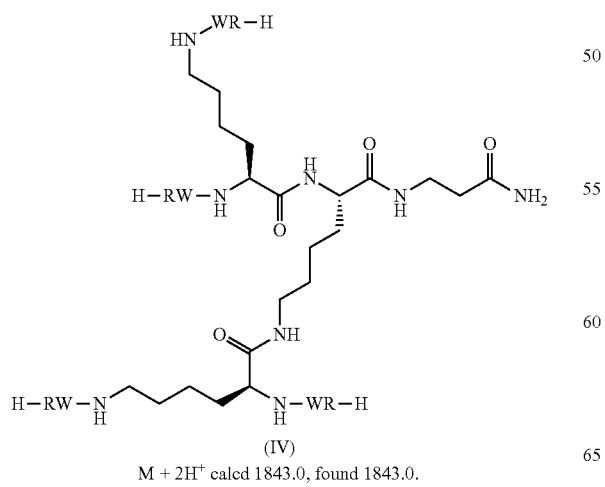

(IV)

M + 2H$^+$ calcd 1843.0, found 1843.0.

Compound 4 [Den(KW)$_{4D}$]

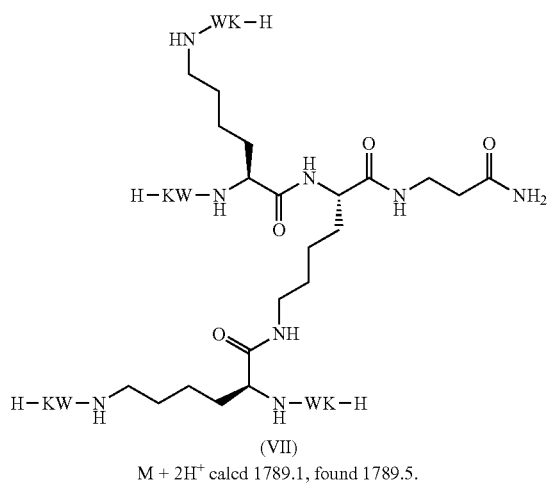

(VII)

M + 2H$^+$ calcd 1789.1, found 1789.5.

Compound 5 [Den(KY)4D]

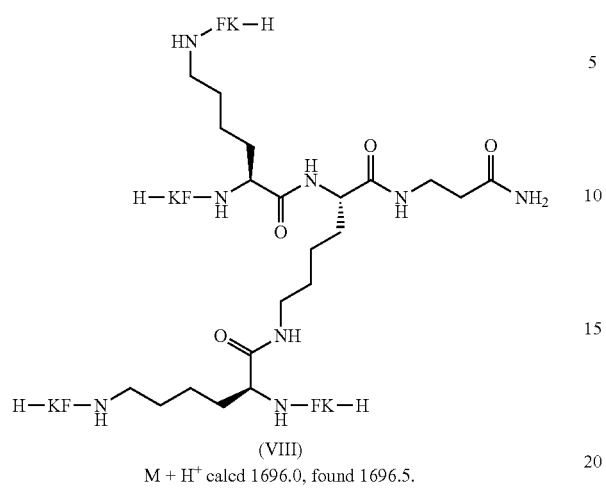

(VIII)
M + H⁺ calcd 1696.0, found 1696.5.

Compound 6 [Den(KF)4D]

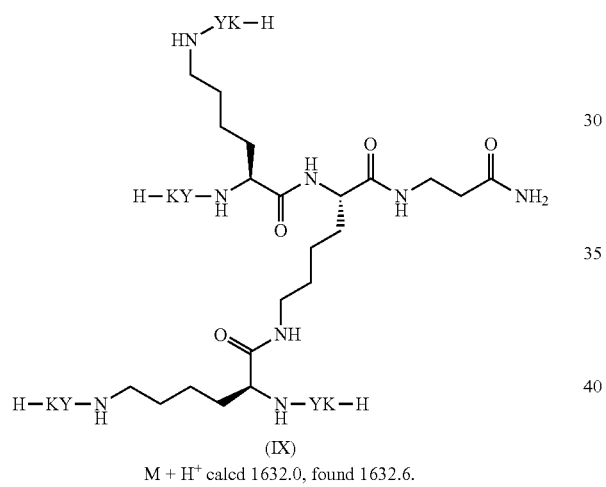

(IX)
M + H⁺ calcd 1632.0, found 1632.6.

Compound 7 [Den(WH)4D]

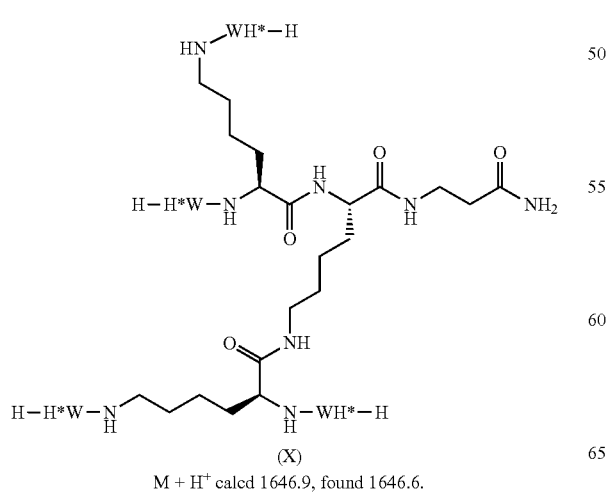

(X)
M + H⁺ calcd 1646.9, found 1646.6.

Compound 8 [Den(R—2NaI)4D]

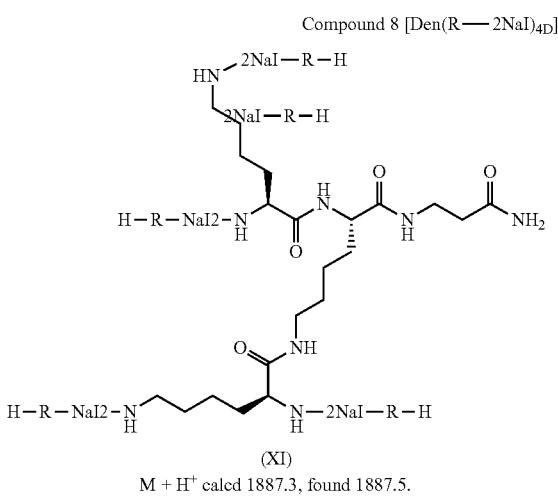

(XI)
M + H⁺ calcd 1887.3, found 1887.5.

Compound 9 [Den(RW*)4D]

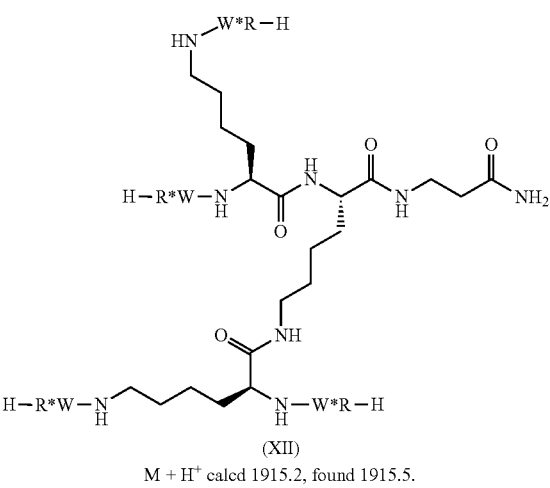

(XII)
M + H⁺ calcd 1915.2, found 1915.5.

In a second synthetic embodiment of the invention, dendrimers having a substitution at the C-terminus, represented by 'Z', can be prepared using the representative synthetic pathway depicted in Scheme 2, below, and by the corresponding procedure.

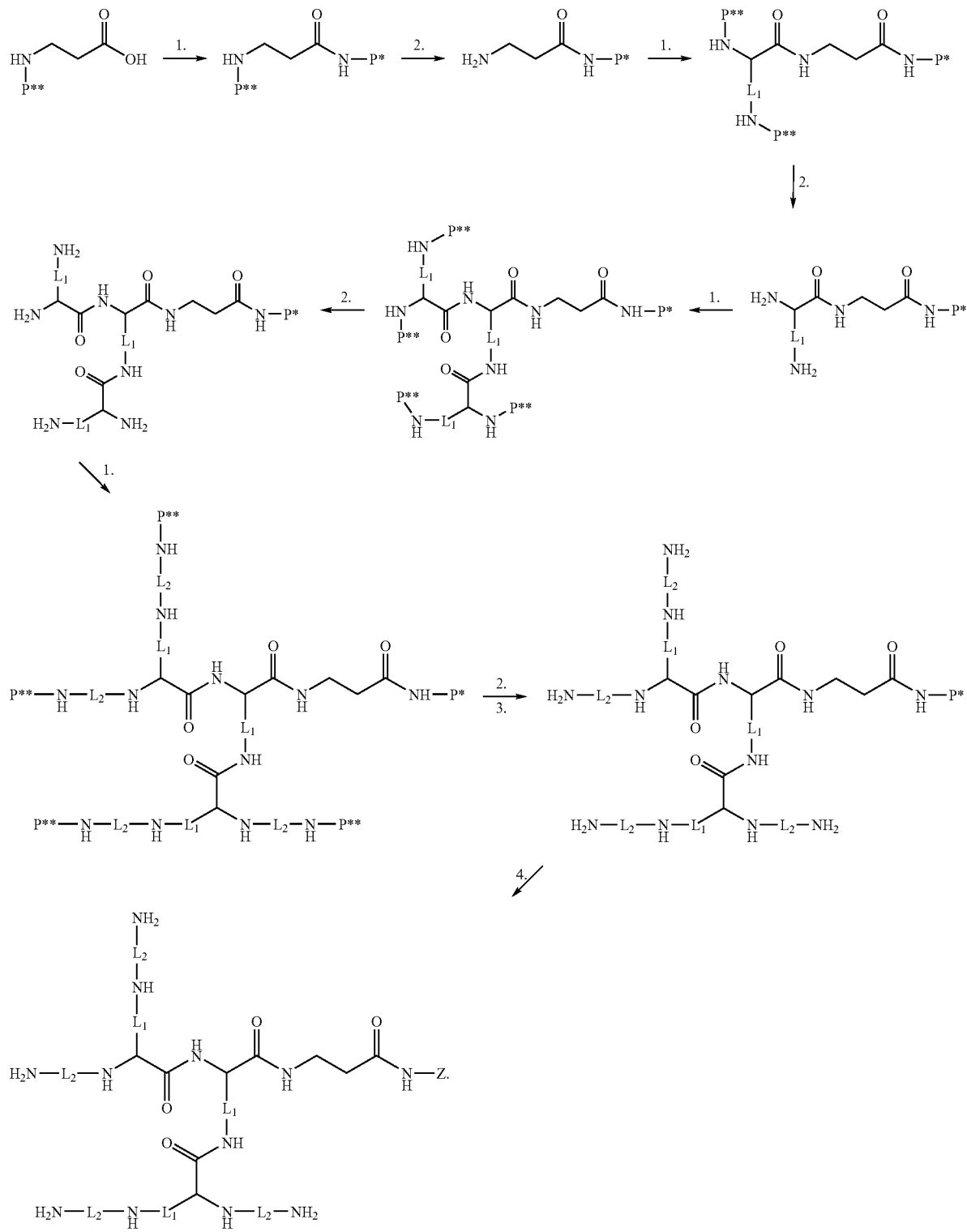
Scheme 2
P*-HMBA-AM resin
P**-Fmoc
Z-Benzyl amine, Benzyl alcohol and Nonylamine
1. HOBt/HBTU/DIEA
2. Piperidine
3. 95% TFA/2.5% TIS/2.5% H₂O
4. 5:5:1, Z/THF/TEA, KCN First, an Fmoc-protected β-alanine residue, making up the C-terminus, was coupled to HMBA-AM resin in the presence of 4 equivalents of DIC (N,N'-diisopropylcarbodiimide) and 0.1 equivalents of DMAP (4-Dimethylaminopyridine). This residue was deprotected and coupled to Fmoc-Lys(Fmoc)-OH with Fmoc-protected α- and ε-amino groups. Using the same protecting group for both amino groups allows for simultaneous deprotection, so that two amide bonds are formed during the next coupling step. The tetravalent core was achieved by repeating this step. In effect, 4 free amino groups were created. Then 4 RW dipeptides were simultaneously coupled to $NH_2$ groups of the lysine core template.

Deprotection/Resin Cleavage.

1.) The peptide-resin is rinsed sequentially and 3 time each with DMF, DCM and diethyl ether. The peptide is then allowed to air dry for about 30 min, and is then dried overnight in a lyophilizer.

2.) The side chain protecting groups are then deprotected using 95:2.5:2.5 TFA/water/triisopropyl silane. This reaction is performed at room temperature with shaking for about 2 hours.

3.) The deprotection solution is then drained into a waste container. The resin is washed sequentially and 3 times each with DMF, DCM, and diethyl ether. The resulting material is allowed to air dry for about 30 min and is thene returned to the lyophilizer to dry overnight.

4.) The transesterification/cleavage reaction is performed at 50° C. and with shaking/stirring over night in the presence of a solution that is 5:5:1 Benzyl amine/tetrahydrofuran (THF)/triethylamine (TEA), Benzyl alcohol/tetrahydrofuran (THF)/triethylamine (TEA) and Nonylamine/tetrahydrofuran (THF)/triethylamine (TEA), respectively, to obtain the above three final products. For every 111 mL of the solution, add about 15 mg of solid KCN is added as a catalyst. This component of the reaction mixture containing the final product is then precipitated in ether and purified on reverse phase HPLC. Molecular weights are verified by MIS, for example, using a Bruker MALDI-TOF spectrometer, which in the present instances, were in agreement with theoretical masses: Compound 10—Den(RW)$_{4D}$-Benzyl amine, M.W.1932.3; Compound 11—Den(RW)$_{4D}$-Benzyl ester, M.W.1933.3; and Compound 12—Den(RW)$_{4D}$-Nonylamine, M.W.1968.5.

The following representative amino acids are used for $L^2$ dipeptide linkers are as set forth with Scheme 1 and Compounds 1-9. The representative groups used for substitution at the position occupied by Z, are as follows:

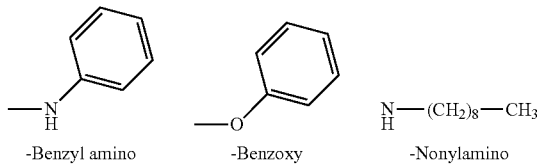

-Benzyl amino    -Benzoxy    -Nonylamino

Compound 10 [Den(RW)$_{4D}$ Benzylamine]

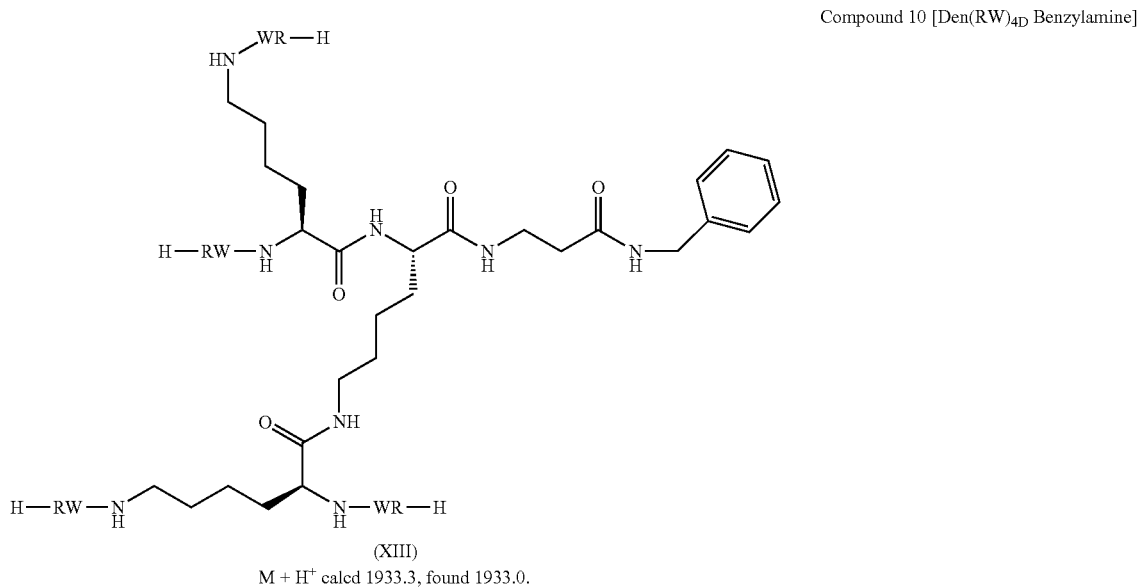

(XIII)

M + H$^+$ calcd 1933.3, found 1933.0.

-continued

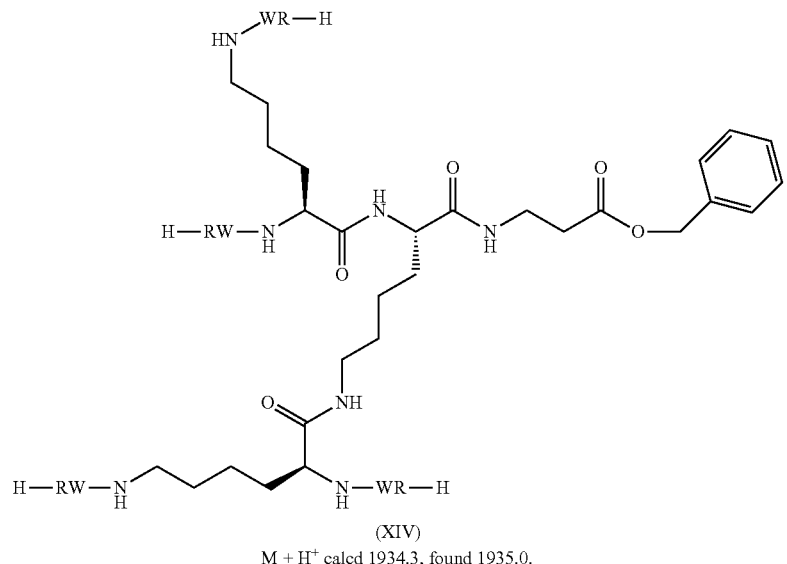

(XIV)

M + H⁺ calcd 1934.3, found 1935.0.

Compound 11 [Den(RW)$_{4D}$ Benzylester]

Compound 12 [Den(RW)$_{4D}$ Nonylamine]

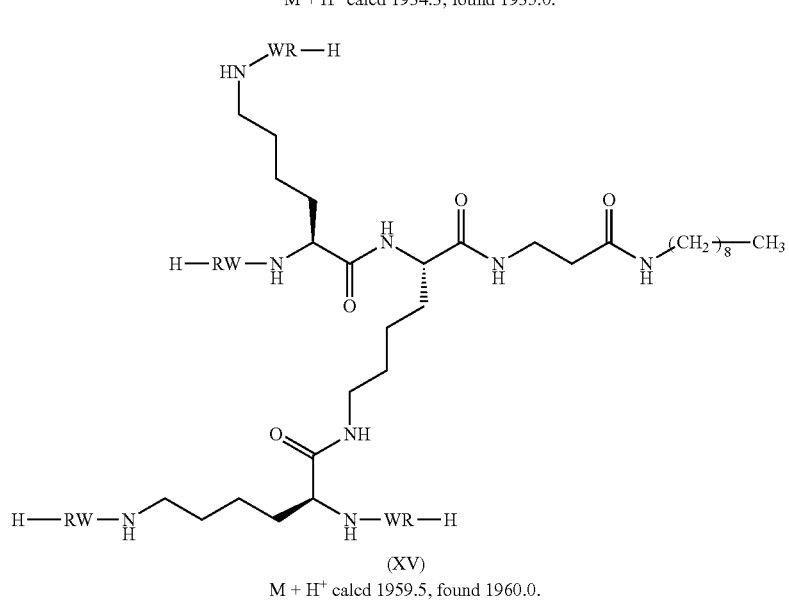

(XV)

M + H⁺ calcd 1959.5, found 1960.0.

EXAMPLES

The following examples are presented in order to more fully illustrate the preferred embodiments of the invention. They should in no way be construed, however, as limiting the broad scope of the invention.

Example 1

Antibacterial Activity

Antibacterial and Hemolytic Assays

The antibacterial activity of each peptide was tested by following standard broth microdilution protocols recommended by the National Committee for Clinical Laboratory Standard (NCCLS 2004). *B. anthracis* (32F2 Sterne) (gift from Dr. Martin Blaser, NYU Medical School); *E. faecalis* (29212), *A. baumanii* (ATCC BAA-747) and *B. Subtilis* (ATCC 6633) were obtained from the American Type Culture Collection (ATCC; Rockville, Md.), respectively. Bacteria were grown in Mueller Hinton Broth (MHB) at 37° C. for overnight. Then, cultures were diluted in MHB to a final concentration of $2 \times 10^4$ to $2 \times 10^5$ CFU/mL. Bacterial inocula were incubated at 37° C. in PBS buffer (high salt, 150 mM NaCl; low salt, 75 mM NaCl), pH 7.2, with varying volumes of 2-fold dilution of peptide stocks. The 18-hour absorbance data were used to calculate the percent inhibition for each sample by comparing with the absorbance of cultures without peptides. Bacterial growth was measured by turbidity as optical density at 600 nm using a Genesys 5 Spectrophotometer (Rochester, N.Y.). All assays were carried out in triplicate.

Hemolytic activity of model peptides was assessed on fresh sheep erythrocytes (Fitzgerald Inc., Concord, Mass.). Peptide concentrations yielding 50% hemolysis were used as hemolytic dose (HD$_{50}$) determined from dose-response curves. The red blood cell suspension was incubated in PBS buffer (pH 7.2) with varying volumes of peptide stocks at 37° C. for 30 minutes, and then spun down at 3,000 rpm for 10 mins. The resulting supernatant was diluted by a factor of 40 in distilled water. The absorbances of the supernatant at λ=540 nm ($OD_{540}$) were measured in the UV Spectrophotometer. Zero hemolysis and 100% hemolysis controls were obtained by incubating the cells with buffer and 1% Triton-X, respectively. Hemolytic index (HI) was defined as $HI=HD_{50}/IC_{50}$.

High Salt Vs Low Salt

Assays of antibacterial activity under various salt concentrations were carried out to simulate salt effects under different physiological conditions. The minimum inhibitory concentrations ($MIC_{50}$) of dendrimer $(RW)_{4D}$, the naturally occurring antimicrobial peptide control, indolicidin and two control antibiotics were determined in no salt, low- (with 75 mM NaCl) and high-salt (with 150 mM NaCl) conditions. Relative to indolicidin, the dendrimer $(RW)_{4D}$ is more active against ampicillin- and streptomycin-resistant E. coli (D31) and multi-drug resistant strain S. aureus in all three salt concentrations. $(RW)_{4D}$, with a mean $MIC_{50}$ of 3.8 μg/ml and 13.6 μg/ml against E. coli and S. aureus respectively, showed a 50% increase in $MIC_{50}$ value from no salt to high-salt condition. By contrast, linear indolicidin showed >100% increase in $MIC_{50}$ under the same conditions (Table 1).

TABLE 1

Salt effect on antibacterial activity of AMPs (μg/ml)

| AMPs | [a] $MIC_{50}$, μg/ml 0 mM NaCl | | [a] $MIC_{50}$, μg/ml 75 mM NaCl | | [a] $MIC_{50}$, μg/ml 150 mM NaCl | |
|---|---|---|---|---|---|---|
|  | E. coli | S. aureus | E. coli | S. aureus | E. coli | S. aureus |
| Den $(RW)_{4D}$ | 3.0 | 10 | 3.9 | 15 | 4.5 | 16 |
| Indolicidin | 24 | 15 | 43 | 20 | 52 | 33 |
| Gentamicin | 1.2 | 51 | 1.2 | 51 | 1.2 | 51 |
| Ceftazidime | 44 | 63 | 44 | 63 | 44 | 63 |

[a] The results are the mean of three independent experiments performed in parallel.

Spectrum of Antibacterial Activity

It has been shown above that dendrimer $(RW)_{4D}$ preferably kills gram-negative bacteria. We further evaluated the range of activity by testing two AMPs and two antibiotics. against three other gram-positive bacteria. The dendrimer $(RW)_{4D}$ displayed a spectrum of activity with a mean $MIC_{50}$ of 7.4 μg/ml against all test organisms. Even though this number is higher than that of indolicidin (3.6 μg/ml), the much lower hemolytic activity of dendrimer $(RW)_{4D}$ makes it a better antimicrobial agent in terms of its selectivity, as evaluated by HI (Table 2A). Furthermore, $Den(KW)_{4D}$, $Den(RY)_{4D}$, $Den(KF)_{4D}$, $Den(KY)_{4D}$, and $Den(RF)_{4D}$ also showed antibacterial activity against E. coli, S. aureus and Acinetobacter. baumannii (ATCC BAA-747) (Table 2B).

The same evaluation was made with respect to $Den(H*W)_{4D}$, $Den(R-2Nal)_{4D}$ and $Den(RW*)_{4D}$, and demonstrated comparable activity with improvements in particular instances, over the results presented in Table 2B. Lastly, the tests performed with $Den(RW)_{4D}$-Benzyl amine, $Den(RW)_{4D}$-Benzyl ester and $Den(RW)_{4D}$-Nonylamine, demonstrated that these C-terminal substituted dendrimers had particularly increased antimicrobial activity.

TABLE 2A

Antibacterial spectrum of $Den(RW)_{4D}$ against some gram-positive bacterial strains (μg/ml)

| AMPs | [a] $MIC_{50}$, μg/ml | | | [b] $HD_{50}$, μg/ml | HI | | |
|---|---|---|---|---|---|---|---|
|  | B. subtilis | B. anthracis | E. faecalis |  | B. subtilis | B. anthrax | E. faecalis |
| $Den(RW)_{4D}$ | 3.5 | 13 | 5.5 | 1410 | 402 | 105 | 256 |
| Indolicidin | 1.0 | 8.2 | 1.6 | 293 | 281 | 35.7 | 181 |
| Gentamicin | 0.32 | 3.1 | 0.36 | >2000 | / | / | / |
| Ceftazidime | 6.2 | 91 | 14 | >2000 | / | / | / |

[a] The results are the mean of three independent experiments performed in parallel.

[b] $HD_{50}$ determined from dose-response curve is peptide concentrations corresponding to 50% hemolysis.

TABLE 2B

Antibacterial spectrum of $Den(RF)_{4D}$, $Den(RY)_{4D}$, $Den(KW)_{4D}$, $Den(KY)_{4D}$, and $Den(KF)_{4D}$ against gram-positive and negative bacterial strains (μg/ml)

| AMPs | [a] $MIC_{50}$, μg/ml | | | [b] $HD_{50}$, μg/ml | HI | | |
|---|---|---|---|---|---|---|---|
|  | E. coli | S. aureus | A. baumannii |  | E. coli | S. aureus | A. baumannii |
| $Den(KW)_{4D}$ | 30.6 | 23.3 | 52 | 1459.3 | 47.69 | 62.63 | 28.06 |
| $Den(RY)_{4D}$ | 12.6 | 45.7 | 193 | 2151 | 170.7 | 47.07 | 11.15 |
| $Den(KF)_{4D}$ | 77 | 145 | 175 | 2500 | 33 | 17 | 14 |
| $Den(KY)_{4D}$ | 84.4 | 240 | 360 | 3740 | 44 | 16 | 10 |
| $Den(RF)_{4D}$ | 30 | 180 | 160 | 2780 | 90 | 15 | 17 |

[a] The results are the mean of three independent experiments performed in parallel.

[b] $HD_{50}$ determined from dose-response curve is peptide concentrations corresponding to 50% hemolysis.

TABLE 2C

Antibacterial activity of Den(HW)4D, Den(R-2Nal)4D and Den(RW*)4D.

| AMPs | [a] MIC$_{50}$, µg/ml | | | [b] HD$_{50}$, µg/ml | HI | | |
|---|---|---|---|---|---|---|---|
| | E. coli | S. aureus | A. baumannii | | E. coli | S. aureus | A. baumannii |
| Den(HW)$_{4D}$ | 30.6 | 43.3 | 82.7 | 1860.2 | 60.8 | 43.3 | 22.5 |
| Den(R-2Nal)$_{4D}$ | 21.5 | 36.0 | 51.3 | 1468.7 | 68.3 | 40.8 | 28.6 |
| Den(RW*)$_{4D}$ | 9.3 | 13 | 35 | 2859.2 | 307.4 | 220.0 | 81.69 |

[a] The results are the mean of three independent experiments performed in parallel.
[b] HD$_{50}$ determined from dose-response curve is peptide concentrations corresponding to 50% hemolysis.

TABLE 2D

Antibacterial activity of Den(RW)4D-Benzyl amine, Den(RW)4D-Benzyl ester and Den(RW)$_{4D}$-Nonylamine.

| Bacterial strains | [a] MIC$_{50}$, µg/ml | | | HI | | |
|---|---|---|---|---|---|---|
| | (RW)$_{4D}$-Benzyl amine | (RW)$_{4D}$-Benzyl ester | (RW)$_{4D}$-Nonylamine | (RW)$_{4D}$-Benzyl amine | (RW)$_{4D}$-Benzyl ester | (RW)$_{4D}$-Nonylamine |
| A. baumannii | 121 | 78.7 | 75.2 | 11.3 | 19.4 | 19.2 |
| B. anthracis | 34.8 | 34.2 | 31.8 | 39.2 | 44.6 | 45.5 |
| E. coli D31 | 21.3 | 29.7 | 26.7 | 64.1 | 51.3 | 54.1 |
| S. aureus | 37.8 | 19.6 | 21.6 | 36.1 | 77.8 | 66.9 |
| E. coli | 12.8 | 14.3 | 15.8 | 106.7 | 106.6 | 91.5 |
| B. subitilis | 5.0 | 6.8 | 6.5 | 273.1 | 224.2 | 222.4 |
| E. faecalis | 5.1 | 6.7 | 5.7 | 267.7 | 227.5 | 253.6 |
| [b] RBC | 1366 | 1524 | 1446 | / | / | / |

[b] MIC$_{50}$ for RBC is HD$_{50}$

Example 2

Degradation or Inactivation of AMPs by Protease

AMPs were incubated with trypsin, either at a constant enzyme concentration for various time intervals or with varied concentrations of trypsin for 1 hr, and the antibacterial activity was then determined using standard broth microdilution protocols with E. coli and S. aureus as the target bacteria.
Proteolytic Stability Trypsin digestion experiments. Dendrimer (RW)$_{4D}$ or indolicidin at the concentration of their MIC$_{50}$ was mixed with trypsin to a series of final trypsin concentrations (200 nm, 400 nm, 600 nm, 800 nm and 1000 nm) in PBS buffer at pH 7.4 in microtubes. Enzymatic digestions were carried out at 37° C. for 1 hr and stopped by adding Type I trypsin inhibitor to the samples. Aliquots were added to 96 well plates containing E. coli or S. aureus. Then MICs were determined by the standard broth microdilution protocols. AMPs without trypsin and trypsin inhibited in various concentrations were used as control. The antibacterial activity of samples is expressed in percentage of that of samples without trypsin treatment (Sieprawska-Lupa et al. 2004).
Results of Trypsin Digestion Experiments Incubation time variation. Dendrimer (RW)$_{4D}$ and indolicidin at the MIC$_{50}$ concentrations are incubated with 1 µM trypsin (maximum concentration tested in above experiments) for various incubating time intervals up to 24 hrs. At selected times, samples were collected and trypsin inhibitor was added to stop the reaction. The antimicrobial activity of each sample against E. coli and S. aureus was assayed in the standard broth microdilution protocols. AMPs without trypsin and in the presence of various concentration of inhibited trypsin were used as controls. The antibacterial activity of samples is expressed in percentage of that of samples without trypsin treatment.

Figure 2:
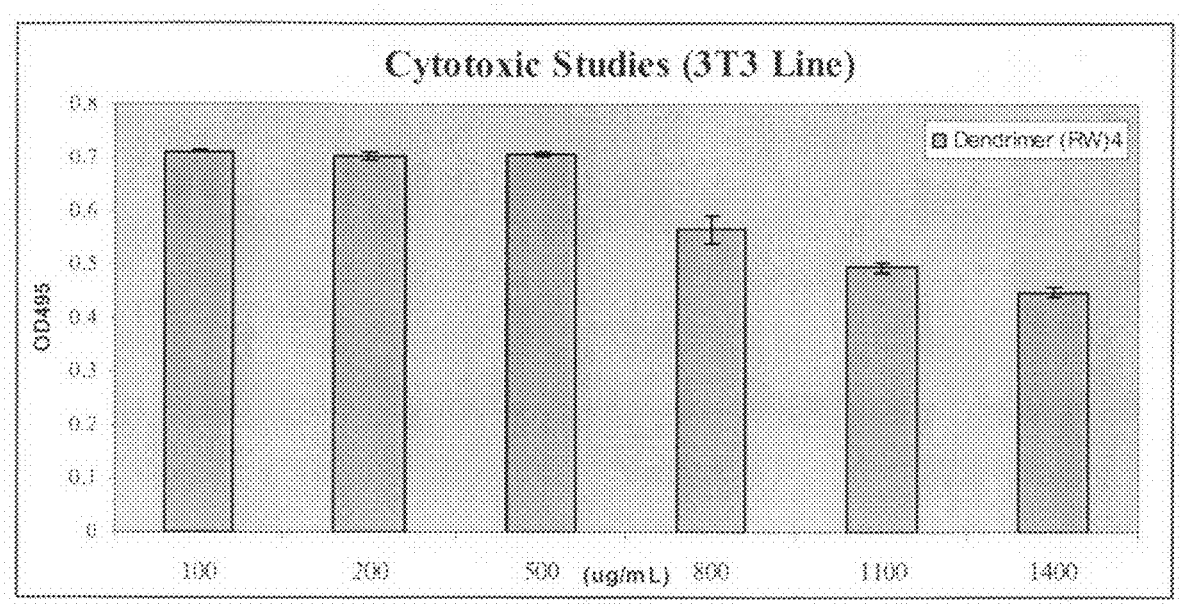
FIG. 2 graphically presents the results of a cytotoxicity assay using a 3T3 mouse fibroblast cell line.

The data from these experiments indicate that trypsin inactivates the antibacterial activity of indolicidin in a time- and concentration-dependent manner (FIG. 1). After indolicidin was treated with 100 nM trypsin for 1 hr or 1 µM trypsin for 2-5 min, its antibacterial activity decreased to 25-30% of the untreated control. By contrast, the antibacterial activity of (RW)$_{4D}$ was resistant to inactivation by trypsin at high concentration, and over various time intervals.
Cytotoxicity Assays Cytotoxicity activity of peptides was assessed on a 3T3 mouse fibroblast cell line. The cells were grown in 96 well plates and a 100 µl aliquot of a three fold serial dilution of the peptides was dispensed into each well. Buffer alone was used as the positive control and H$_2$O$_2$ was used as the negative control. MTS (metallothionein) was added to each well prior to incubation to visualize the cells. The cells were incubated for 24 hours and their absorbance were measured at λ=495 nm.
Cytotoxicity Results Some cationic AMPs are very highly toxic to mammalian cells, e.g., bee venom melittin, whereas others show little or no acute cytotoxicity (Hancock and Diamond 2000). We assayed the cytotoxic activity of peptides on a 3T3 mouse fibroblast cell line with favorable results. The IC$_{50}$ is approximately 1381 µg/mL for the dendrimer (RW)$_{4D}$ (FIG. 2), indicating that multivalent AMPs have low cytotoxicity.
Dye Leakage Assay To confirm that the multivalent AMPs interact with and disrupt phospholipid bilayers, we measured the ability of dendrimer (RW)$_{4D}$ to induce leakage of calcein, entrapped within the interior of large unilamellar vesicles of model membrane POPG (1-Palmitoyl-2-Oleoyl-sn-Glycero-3-[Phospho-rac-(1-glycerol)]) with negatively charged head group. The leakage of vesicle contents to the AMPs was monitored by the release of calcein encapsulated in large unilamellar vesicles. The method of preparation of dye-encapsulated vesicles has been reported in detail (Torchilin and Weissig 2003). In short, large unilamellar POPG vesicles were prepared by reverse-phase evaporation. After evaporating the organic solvent, residue were hydrated with the calcein solution (100 mM) in buffer (10 mM Tris-HCl pH 7.4). The free calcein was removed by eluting through a Sephadex G-50 size-exclusion column in the same buffer. The leakage process was monitored by following the increase of calcein fluorescence intensity at 515 nm (excitation at 490 nm) after 20 μL of AMPs at different concentrations were added to 10 μL of vesicle solution mixed in 2 mL of TBS buffer. Complete leakage was achieved by addition of 100 uL of 20% Triton X-100 to the 2 ml solution, and the corresponding fluorescence intensity was used as 100% leakage for the calculation of leakage fraction.

Figure 3:
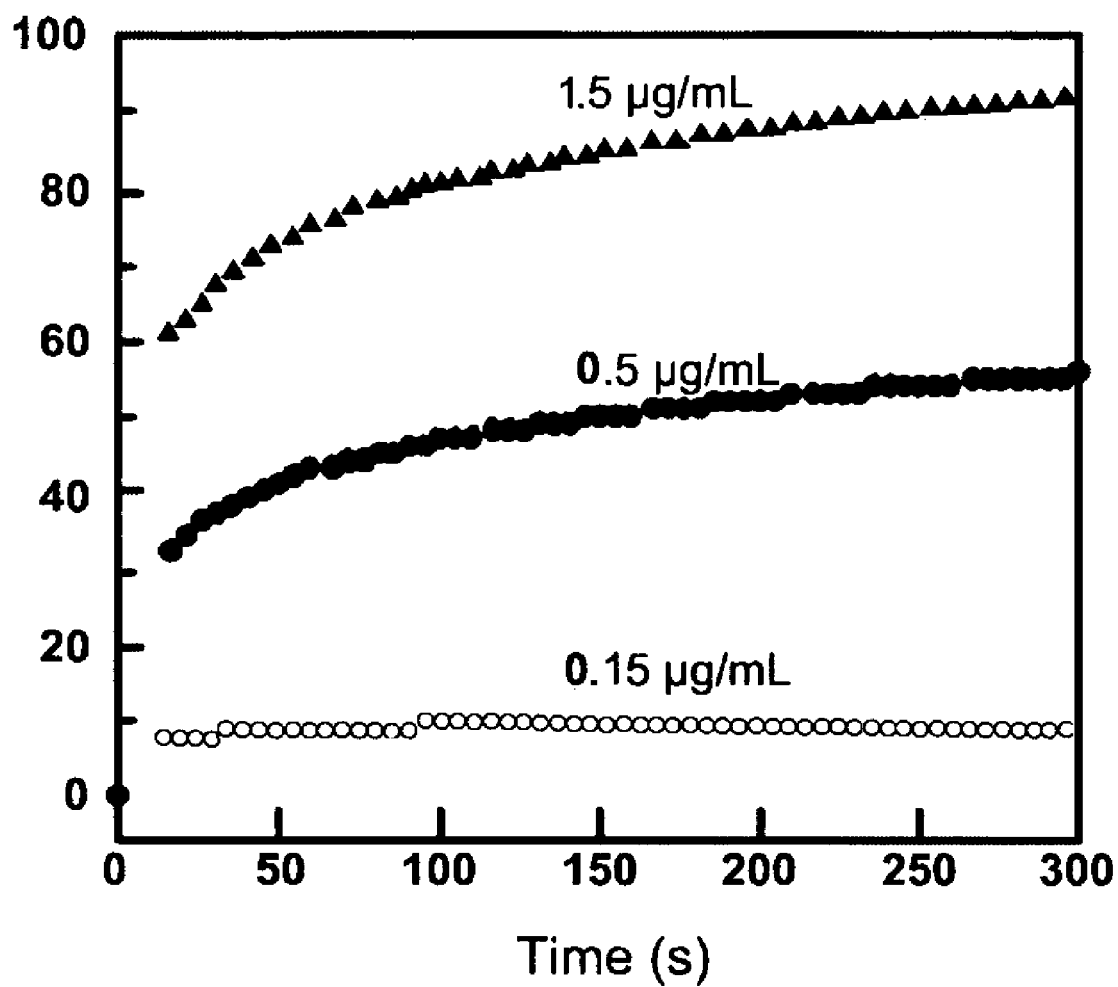
FIG. 3 graphically depicts the results of the measurement of the ability of dendrimer $(RW)_{4D}$ to induce leakage of calcein, entrapped within the interior of large unilamellar vesicles of model membrane POPG. The extent of leakage of encapsulated calcein was detected by its fluorescence at 515 nm, with 100% leakage calibrated by addition of 0.2% Triton X-100.

The extent of leakage of encapsulated calcein caused by peptides was detected by its fluorescence at 515 nm (FIG. 3). The result is that $(RW)_{4D}$ caused calcein leakage in a concentration-dependent manner. The concentration at which peptide caused 50% dye leakage was 0.5 μg/ml, approximately 30-fold lower than the $MIC_{50}$ values for S. aureus.

Example 3

Computational Simulation for Studying Mechanism of Dendrimer $(RW)_{4D}$

Molecular dynamics (MD) simulations were carried out on dendrimer $(RW)_{4D}$ in an n-octane/water interfacial system. In the present work, the core of dendrimer is polyamidoamine instead of trilysine core (Han et al. 2005). The initial conformations were randomly generated and equilibrated in aqueous solution. The starting position of dendrimer molecules was located at the interface of n-octane/water. The whole system then contained 301 n-octane and 2674 water molecules, and 8 chloride ions, totally 16104 atoms in a 50×50×60 angstrom^3 box. Sampling was over 2 ns in an isothermal-isobaric ensemble at T=300 K and P=1 atm. The MD simulations were preformed with Amber 8 molecular dynamics package (Case et al. 2004).

Figure 4:
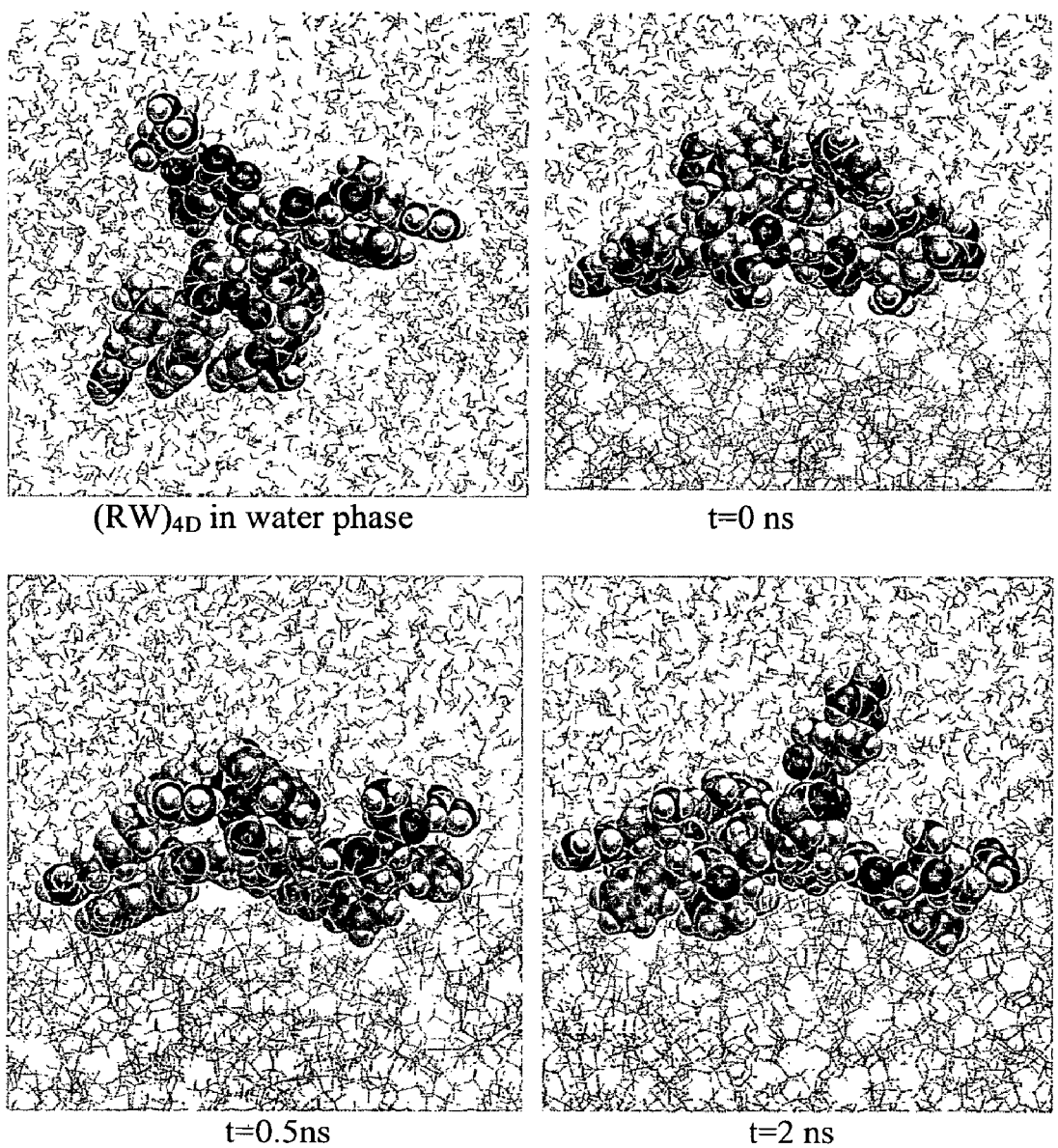
FIG. 4 presents the dynamic evolution of the dendrimer $(RW)_{4D}$ as monitored with MD in the isothermal-isobaric ensemble at T=300 K and P=1 atm. Color notation: n-octane (green); water (oxygen: red; hydrogen: white); $(RW)_{4D}$: carbon (green), oxygen (red), nitrogen (blue), and hydrogen (white).

MD simulations were carried out on dendrimer $(RW)_{4D}$ in a n-octane/water interfacial system. It was found that, in the water phase, four branches spread out of the core of the dendrimer, and that Arg/Trp residues in the same branch lie close to each other via cation-λ interactions. Hydrophobic interactions between Trp residues can also be observed. In such a conformation, once the multivalent AMPs were moved to the interface, they rapidly exposed the polar guanidine groups into the water with the indole ring side chains into the n-octane phase (FIG. 4).

Example 4

Summary for the Inhibition of E. Coli Biofilm Formation by Poly-Peptides

Biofilm Assay:

E. coli RP437 was used to form biofilms on ¼×½ inch stainless steel coupons. The overnight E. coli culture grown in LB was used to inoculate the biofilm cultures to $OD_{600}$ of 0.05 as measured by a Genesis 5 Spectrophotometer (Spectronic Instruments, Rochester, N.Y.). The stainless steel (S.S.) coupons were polished using a fine 3M SandBlaster sandpaper, then autoclaved for sterilization. The S.S. coupons were incubated in a plastic petri dish (60×15 mm) containing 7 mL LB medium supplemented with hexamer or dendrimer (25 μg/mL and 50 μg/mL) respectively at 37° C. without shaking for 24 hours. For all the treatments, duplicate coupons were tested.

Figure 5:
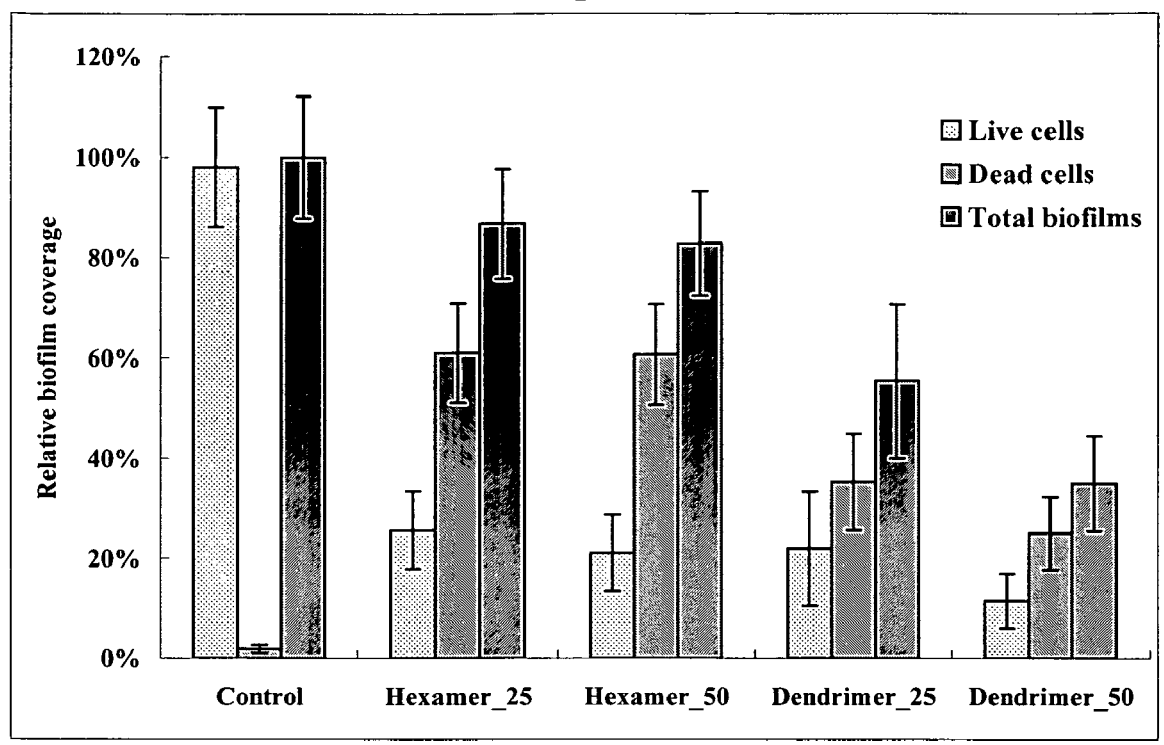
FIG. 5 graphically presents the summary of a biofilm assay for the inhibition of E. coli biofilm formation by poly-peptides, and shows relative biofilm coverages for live cells, dead cells, and total biofilms. All the data were normalized based on the coverage of total biofilms of control samples.
Figure 6:
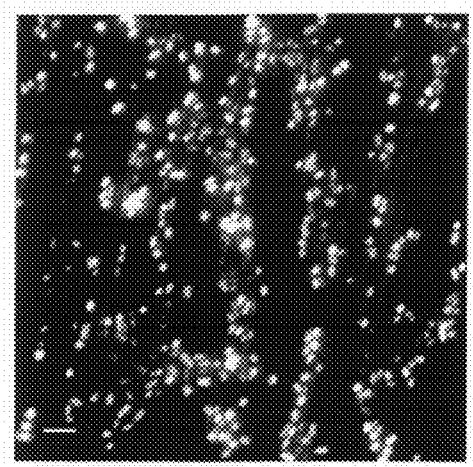
FIG. 6 comprises five representative fluorescence microscope images: (the scale bar=5 µm), depicting the results of the biofilm assay of Example 4.
Figure 6:
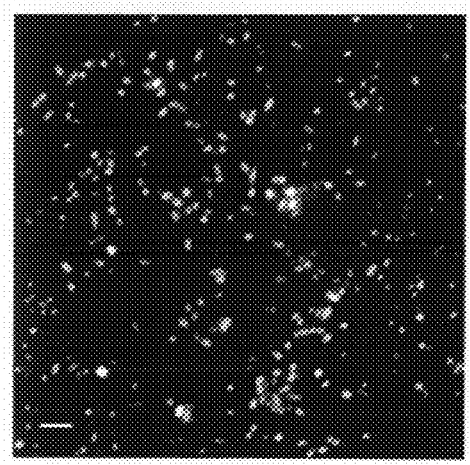
Figure 6:
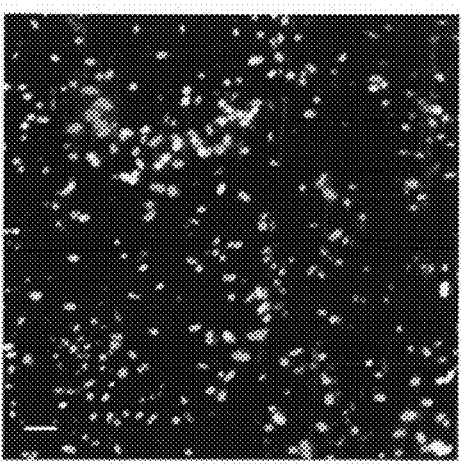
Figure 6:
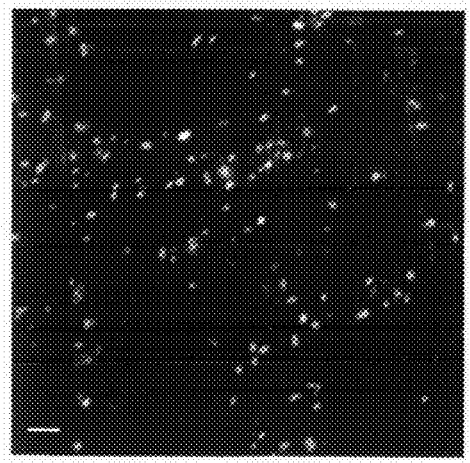
Figure 6:
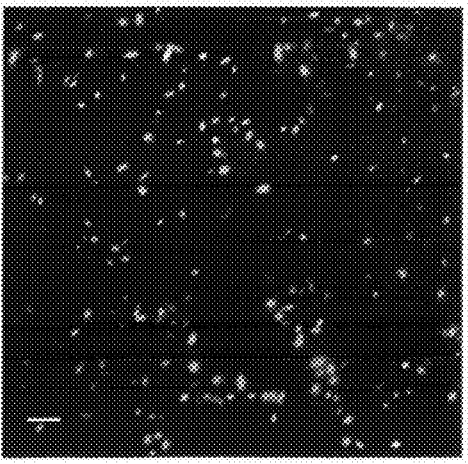

Staining Assay:

To analyze the E. coli biofilms using fluorescence microscopy, the biofilms were stained with LIVE/DEAD BACLIGHT™ bacterial viability kit (Cat# L7012, Invitrogen Corporation, California). Each S.S. coupon was washed gently by dipping vertically in 0.85% NaCl buffer three times (change to fresh buffer after each dipping). Then, they were soaked in 1 mL of 0.85% NaCl buffer containing 3 μl of staining component A and B (1:4) in the dark for 15 mins. Images were taken by AXIO Imager.M1 (Carl Zeiss, German). Five images were taken for each sample. Data were obtained and are presented in Table 3, below, as well as in FIG. 5.

TABLE 3

| | | Biofilm coefficients | | |
| --- | --- | --- | --- | --- |
| | | Live cells | Dead cells | Total biofilms |
| Blank control | | 19.76% ± 2.39% | 0.37% ± 0.16% | 20.16% ± 2.44% |
| Hexamer | 25 μg/mL | 5.18% ± 1.57% | 12.29% ± 2.00% | 17.49% ± 2.20% |
| | 50 μg/mL | 4.25% ± 1.55% | 12.22% ± 2.02% | 16.68% ± 2.11% |
| Dendrimer | 25 μg/mL | 4.42% ± 2.30% | 7.11% ± 1.93% | 11.16% ± 3.09% |
| | 50 μg/mL | 2.32% ± 1.12% | 5.05% ± 1.47% | 7.06% ± 1.91% |

Note:
Means (±standard deviation) with the same letter are not significantly different. All the statistical analysis was conducted by SAS 9.1.

Results and Conclusions:

1. Both the hexamer and dendrimer showed significant decrease of live cells and increase of dead cells in E. coli biofilms formed on stainless steel coupons.

2. Total biofilm formation was significantly reduced by 50 μg/mL of hexamer compared with blank control, while 25 μg/mL of hexamer was not significant (based on ANOVA analysis).

3. Total biofilm formation was significantly reduced by 25 μg/mL and 50 μg/mL of dendrimer compared with blank control (ANOVA results)

3. The properties of biofilm inhibition by the hexamer and the dendrimer can be described as follows:

Live cells: control<25 μg/mL hexamer≈50 μg/mL hexamer≈25 μg/mL dendrimer<50 μg/mL dendrimer ("≈" means the data is not statistically significant).

Total biofilms: control≈25 μg/mL hexamer≈50 μg/mL hexamer<25 μg/mL dendrimer<50 μg/mL dendrimer Maximum thickness of the biofilms were not significantly different (all were around 10 μm)

Based on the results, it can be concluded that both the hexamer and the dendrimer can greatly reduce live cells in E.

coli biofilm on stainless steel coupons. The dendrimer showed better biofilm inhibition properties than the hexamer in this environment.

Example 5

CFU Assay to Study the Inhibition of *E. Coli* RP437 Biofilms by Peptides

Twenty-four hour biofilms of *E. coli* RP437 were grown on stainless steel coupons in LB medium containing up to 100 μg/mL of the three antimicrobial peptides—dendrimer, hexamer, and octamer. CFU counts were used to determine the extent of inhibition. The procedure of the study is as follows.
Method.

Overnight cultures of *E. coli* RP437 grown in LB medium were used to inoculate 5 mL of LB supplemented with up to 100 μg/mL of each peptide and polished, sterile 316L stainless steel coupons (1.2 cm×0.6 cm×0.1 cm). The cultures were incubated at 37° C. for 24 hours. The coupons were then removed from the bacterial culture using sterile forceps and washed three times in 0.85% NaCl buffer and placed in round-bottom tubes containing 3 mL of fresh NaCl buffer. These were then sonicated for 1.5 minutes in a water bath. The NaCl buffer containing bacterial cells was serially diluted and 60 μL of 1000 and 5000 fold dilutions were plated on LB agar plates. The plates were incubated at 37° C. overnight. The number of CFUs for each sample was counted after incubation. The experiment was conducted in duplicate.
Results.

Figure 7A:
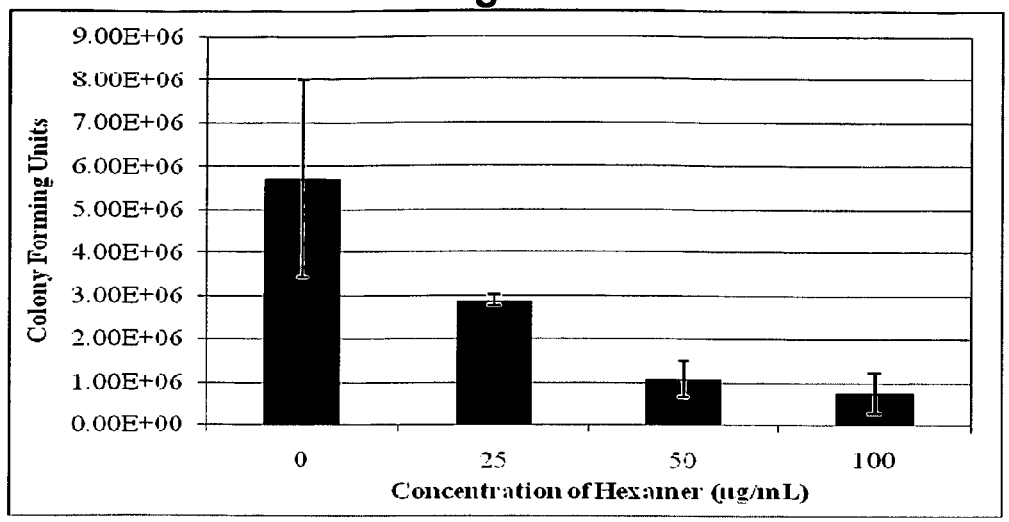
FIGS. 7A-7C comprises three bar graphs indicating the number of viable biofilm cells of E. coli RP437 that developed in up to 100 µg/mL of hexamer (A), octamer (B), and dendrimer (C). Biofilms were inoculated at a starting OD of 0.05 and incubated at 37° C. for 24 hours.
Figure 7B:
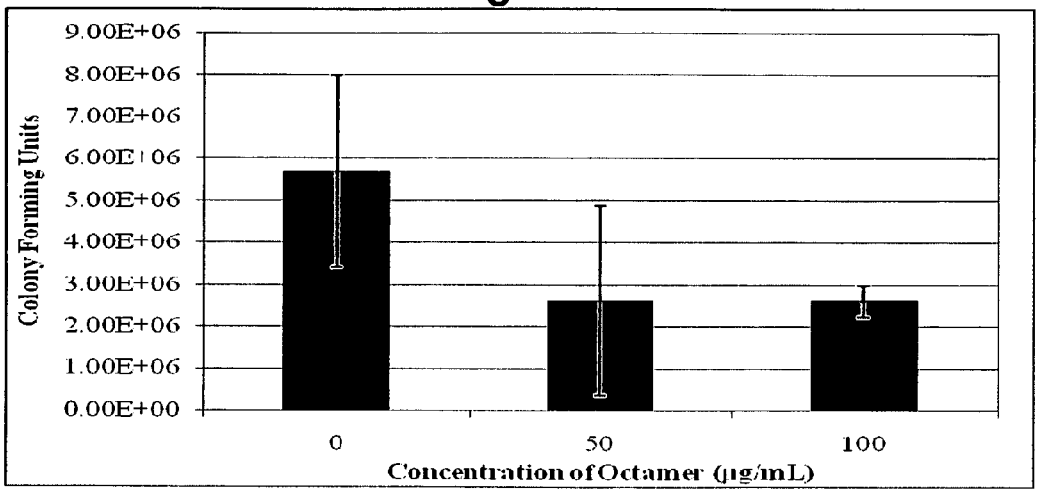
Figure 7C:
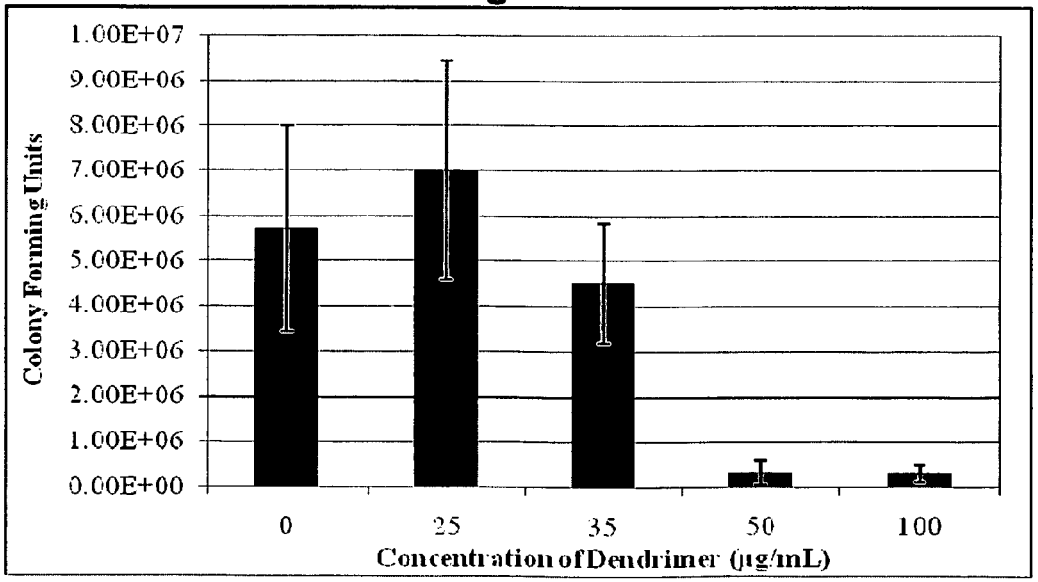

At higher concentrations, the dendrimer was most effective in inhibiting *E. coli* biofilm, while the octamer was least effective. At 50 μg/mL of the hexamer, octamer, and dendrimer, the *E. coli* viable biofilm cell counts were reduced by 81%, 54%, and 94%, respectively. Consistently, 100 μg/mL of the hexamer, octamer, and the dendrimer reduced the biofilm viable cell counts by 87%, 54%, and 95%, respectively. The hexamer was most effective in biofilm inhibition at lower concentrations of 25 μg/mL with 49% biofilm reduction. Although most effective at higher concentrations, the dendrimer was ineffective at 25 μg/mL and reduced viable biofilm cell counts by 21% in 35 μg/mL. Bar charts representing *E. coli* biofilm inhibition by each of the peptides are shown in FIGS. 7A-C.

Example 6

Effect Against Multi-Drug Resistant Bacteria

Figure 8:
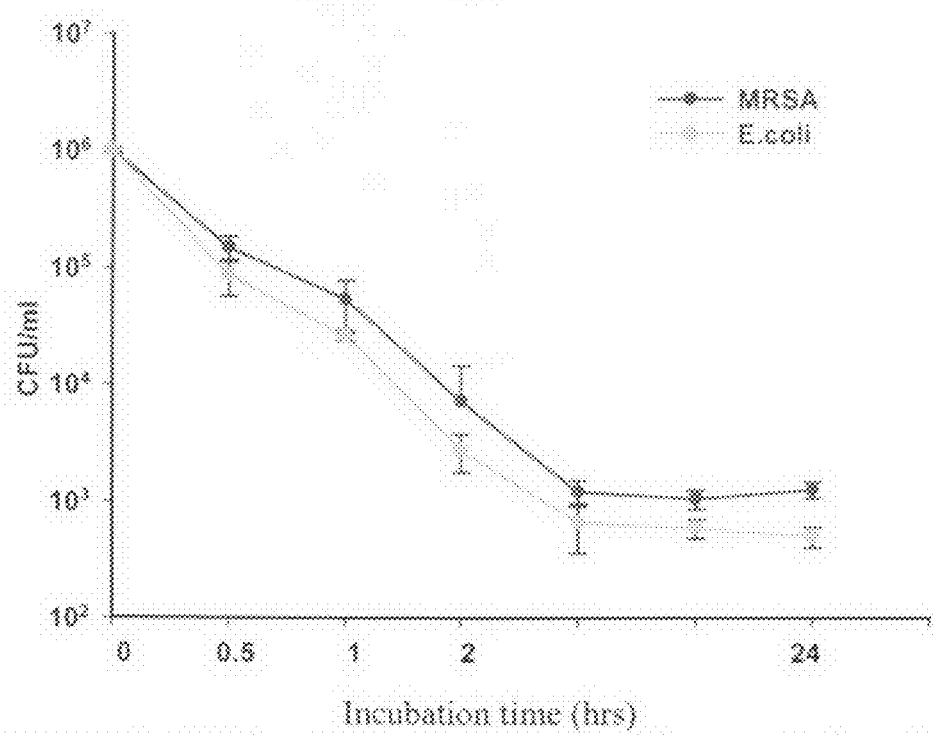
FIG. 8 is a graph presenting the results of a bioassay of a dendrimer of the invention against both gram-positive and gram-negative bacteria that are multi-drug resistant, demonstrating rapid effectiveness of the dendrimer.

A dendrimer prepared in accordance with the invention was tested against multi-drug resistant MRSA gram-positive bacteria, and *E. coli*(D31) gram-negative bacteria. The results of the tests demonstrate a 3-log decrease in bacteria remaining after contact with the dendrimer (RW)$_{4D}$ for one hour, and shows that the dendrimer could rapidly kill multidrug resistant gram-positive MRSA and gram-negative *E. coli*(D31) resistant bacteria. The results are graphically presented in FIG. 8.

Figure 9:
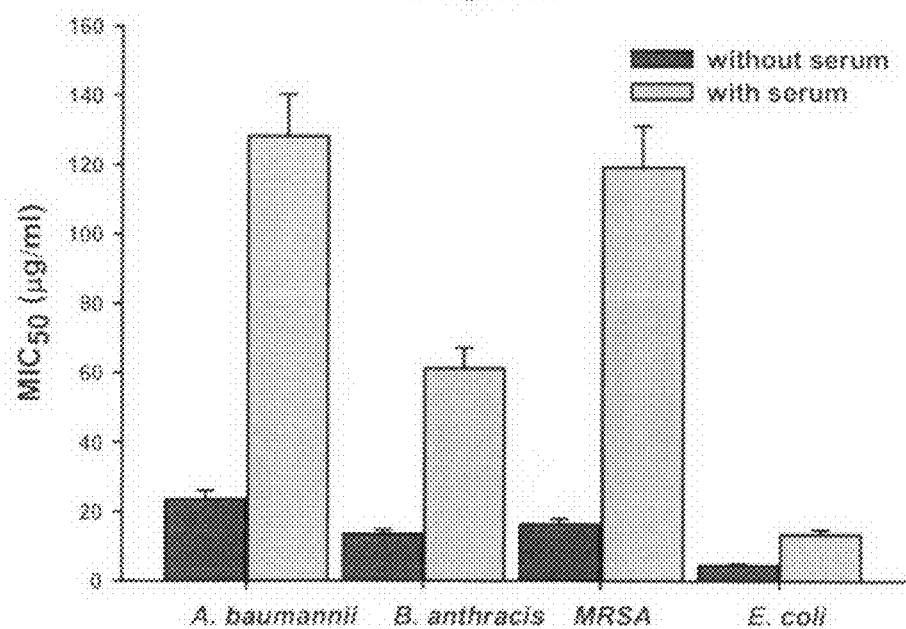
FIG. 9 is a graph presenting the results of an antibacterial assay conducted under physiological conditions, further demonstrating the activity of a dendrimer of the invention.

In a further experiment, antibacterial activity under physiological conditions was tested. The MIC$_{50}$ was determined in the presence of 90% human serum, respectively. The results of this test are depicted in FIG. 9, and demonstrate that human serum cannot completely block the antimicrobial activity of (RW)$_{4D}$. This suggests that dendrimers of the invention such as (RW)$_{4D}$ may have potential application as an injectable drug, and would not be limited to topical applications.

Figure 10A:
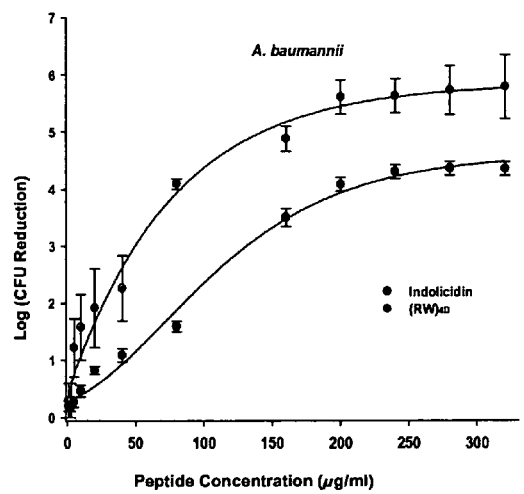
FIGS. 10A and 10B graphically present the results of a dendrimer of the invention against the gram negative bacteria *Acineto Baumannii*.
Figure 10B:
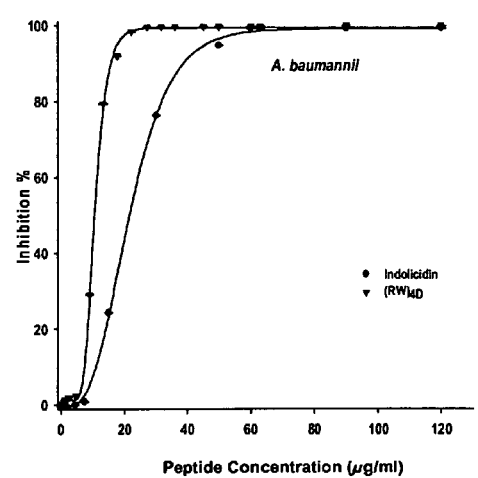

The gram-negative bacteria, Acineto Baumannii, can cause infections, fever and pneumonia and is becoming another serious problem in hospitals and nursing homes. The so-called superbug is very drug-resistant to conventional antibiotics. In the data presented in FIGS. 10A and 10B, it is demonstrated that (RW)$_{4D}$ can kill the bacteria and inhibit its growth at very low concentration.

Figure 11:
FIG. 11 is four plates of *A. Baumannii* cells stained to visually demonstrate the killing ability of the dendrimer of the invention, as set forth in the data in FIGS. 10A and 10B.
Figure 11:
Figure 11:
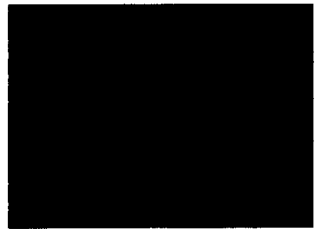
Figure 11:

Additional testing included Live/Dead staining depicted in FIG. 11. The LIVE/DEAD staining assay demonstrates the membrane disturbing activity of (RW)$_{4D}$ in vivo. After 1 hr incubation with 10 uM (RW)$_{4D}$, both gram-positive MRSA and gram-negative *A. baumannii* cells show damaged membranes in red color because of staining with the membrane impermeable red fluorescent nucleic acid stain propidium iodide. Bacteria with intact membranes are stained with the membrane permeable green fluorescent nucleic acid stain SYTO 9. By contrast, vancomycin did not actively kill multidrug resistant MRSA and *A. baumannii*.

Example 7

Figure 12A:
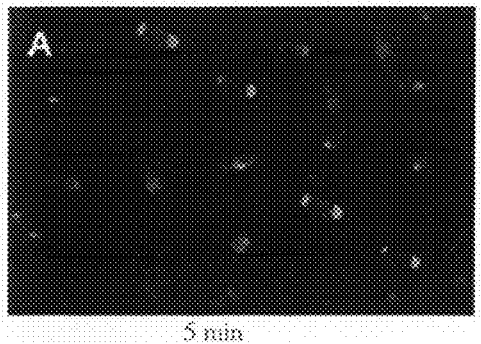
FIGS. 12A and 12B are photomicrographs presenting a visualization of membrane permeation by rhodamine-labeled $(RW)_{4D}$, using confocal laser scanning microscopy.
Figure 12B:
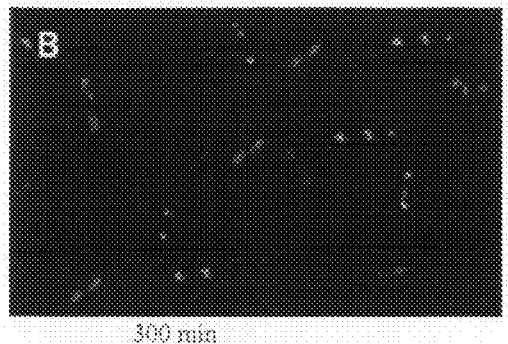

In this further test, visualization of membrane permeation presented in FIGS. 12A and 12B, was demonstrated by rhodamine-labeled (RW)$_{4D}$, using confocal laser scanning microscopy, showed that (RW)$_{4D}$ entered *E. coli* cells after 5 min of incubation and clustered in discrete patches, often situated at the cell poles. There were no significant differences between *E. coli* images taken after 5 and 300 min of incubation with 40 nM (RW)$_{4D}$. This suggests that dendrimers such as (RW)$_{4D}$ have potential to serve as lead compounds for molecular design of antibiotics attacking negatively charged intracellular targets other than the membrane, such as DNA and RNA.

Example 8

Figure 13A:
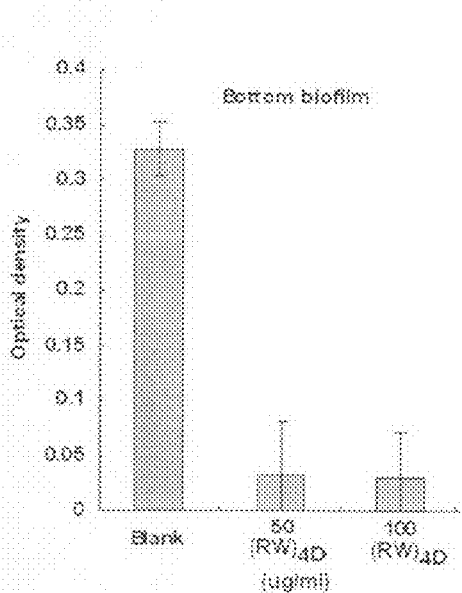
FIGS. 13A and 13B are graphs presenting the results of tests of the effect of dendrimers of the invention on E. coli biofilm formation.
Figure 13B:
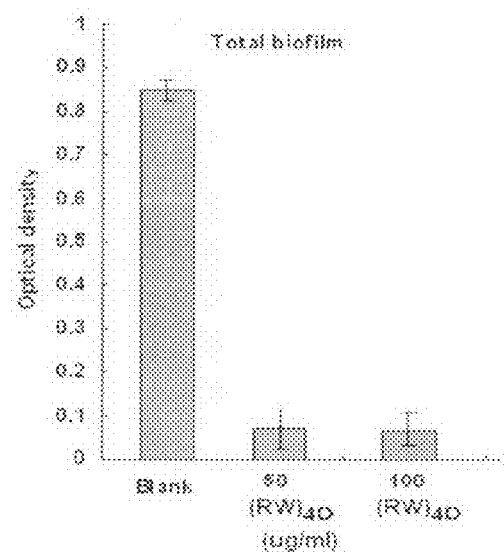

The effect of dendrimers of the invention on *E. coli* biofilm formation was further examined and measured. The development of a bacterial biofilm allows for the bacteria to become more antibiotic resistant. To test whether dendrimeric (RW)$_{4D}$ has effect on biofilm formation, *E. coli* (RP437) was used to form biofilms in 96 well plates with and without different concentrations of peptides. Results showed (RW)$_{4D}$ exhibited inhibition of *E. coli* biofilm formation. Assay summary: *E. coli* (RP437) was used to form biofilms in 96 well plates with and without different concentrations of peptides. After 24 hours incubation, the plates with biofilms were washed and dried 0.1% crystal violet was added to each well and incubated for 20 min after extra dye was removed, OD$_{540}$ was measured to quantify the biofilms on the bottom of wells. Then 95% ethanol was added into each well and OD540 was measured to quantify the total biofilm. The results are graphically presented in FIGS. 13A and 13B.

Example 9

*E. coli* biofilm inhibition by (RW)$_{4D}$ was also studied on stainless steel coupons. Microscope images were taken after staining the two-day biofilms with Live/Dead staining solution. The images shows the total biofilm formation on stainless steel coupons was significantly reduced by 25 μg/mL (RW)$_{4D}$ compared with blank control. Assay summary: *E. coli* RP437 was used to form biofilms in a plastic dish with stainless steel coupons and different concentrations of peptides. After 48 hours incubation, coupon was soaked in NaCl buffer containing staining component in the dark for 15 mins. The results are visually presented in FIGS. 14A and 14B.

Example 10

In this example, the compounds of this invention are shown to be capable of use in the formulation of peptide hydrogels to create sterilized synthetic extracellular matrix (ECM) scaffolds. First, dendrimeric peptides are dissolved in sterile $H_2O$ to a concentration of 4 wt %. Aliquots (75 mL) of peptide stock were added to desired wells in a 48 well tissue culture plate (Costar 3548). DMEM (cell culture media medium) (75 mL, serum-free) was added to the same wells and the solution (2 wt % in peptide) was incubated for several hours to allow the gel to set. The resultant gels were equilibrated to cell culture conditions by addition of DMEM (200 mL) and incubation at 37° C. and 5% $CO_2$ overnight. This media (200 mL) is removed prior to addition of cells. The results of resistance studies establishing the activity of the formed hydrogels are presented in FIGS. 15 A and 15B.

Multidrug-resistant gram-positive S. aureus and gram-negative E. coli (D31) did not show resistance to Den(RW)$_{4D}$ over 250 generations, and maintained the same $MIC_{90}$ value.

Discussion

The above disclosure corresponds to the objectives of the inventors, to focus on the study of a group of unstructured antimicrobial peptides (AMPs), in part because they lack specific structural constraints and adopt a more extended structure, but also because they are composed of a high frequency of certain amino acids, including Trp (W), Phe (F), Lys (K), Arg (R) and Tyr (Y) (van't H of et al. 2001).

Propensity studies of amino acids in membrane proteins suggest that the residues lysine, arginine, tyrosine and tryptophan occur more frequently at the terminal regions of transmembrane helices (Schiffer et al. 1992; Vonheijne 1992; Reithmeier 1995; Wimley and White 1996; Braun and von Heijne 1999; Ridder et al. 2000). It is suggested that these aromatic or charged residues serve to anchor membrane-spanning proteins at interfacial regions in the membrane (Schiffer et al. 1992; Reithmeier 1995; Killian and von Heijne 2000; de Planque and Killian 2003). Indeed, these residues, tend to line the hydrophilic-hydrophobic membrane interface (Deisenhofer and Michel 1989; Henderson et al. 1990; Meers 1990; Chattopadhyay and McNamee 1991; Hu et al. 1993). Trp residues might be involved in the translocation of protein through the membrane. Following translocation, Trp residues could serve as anchors on the periplasmic side of the membrane, an important feature for membrane protein activity (Hu et al. 1993; Ketchem et al. 1993; Koeppe et al. 1994), selectivity (Bogusz et al. 1992; Durell and Guy 1992), folding and assembly (Schiffer et al. 1992). Positively charged Lys and Arg residues predominantly occur in cytoplasmic loops (Schiffer et al. 1992; Vonheijne 1994) (Landoltmarticorena et al. 1993) and are proposed to "snorkel" to the membrane surface where they can interact with the phosphate groups of phospholipid head groups (Mishra et al. 1994; Strandberg and Killian 2003).

To mimic the structural features of some unstructured AMPs and membrane binding proteins, a series of dendrimeric dipeptides presented herein, were designed with combinations of one lipophilic (bulky) amino acid and one positively charged amino acid. Accordingly, the dendrimeric antimicrobial peptide Den(RW)$_{4D}$, Den(RF)$_{4D}$, Den(RY)$_{4D}$, Den(KW)$_{4D}$, Den(KY)$_{4D}$, and Den(KF)$_{4D}$ display the four branched dipeptides with balanced numbers of positively charged and hydrophobic side chains: RW, RF, RY, KW, KY, and KF (see scheme 1), emerging as the best candidates among our de novo designs for potent AMPs. These products are relatively small in size and easily synthesized compared to natural or synthetic AMPs in many other studies. This feature lowers the manufacturing cost and facilitates chemical synthesis in large quantities.

From the above data, it can be seen that these dendrimeric AMPs show potent broad-spectrum antibacterial activity with resistance to high salt inhibition and protease digestion, low cytotoxity, the ability to inhibit the formation of unwanted microbial biofilms, and to show efficacy against multi-drug resistant microbes. The results of this research together with further lead optimization is anticipated to provide novel antibacterials for therapeutic use against multi-drug-resistant bacterial strains.

REFERENCES

Bogusz, S., Boxer, A., and Busath, D. D. 1992. An Ss1-Ss2 Beta-Barrel Structure for the Voltage-Activated Potassium Channel. *Protein Engineering* 5: 285-293.

Braun, P., and von Heijne, G. 1999. The aromatic residues Trp and Phe have different effects on the positioning of a transmembrane helix in the microsomal membrane. *BIOCHEMISTRY-US* 38: 9778-9782.

Case, D. A., Darden, T. A., Cheatham, T. E., Simmerling, I., C. L., Wang, J., Duke, R. E., Luo, R., Merz, K. M., Wang, B., Pearlman, D. A., et al. 2004. AMBER 8, University of California, San Francisco. http://amber.scripps.edu/.

Chattopadhyay, A., and McNamee, M. G. 1991. Average Membrane Penetration Depth of Tryptophan Residues of the Nicotinic Acetylcholine-Receptor by the Parallax Method. *BIOCHEMISTRY-US* 30: 7159-7164.

de Planque, M. R. R., and Killian, J. A. 2003. Protein-lipid interactions studied with designed transmembrane peptides: role of hydrophobic matching and interfacial anchoring (Review). *Molecular Membrane Biology* 20: 271-284.

Deisenhofer, J., and Michel, H. 1989. The Photosynthetic Reaction Center from the Purple Bacterium *Rhodopseudomonas-Viridis*. *Science* 245: 1463-1473.

Durell, S. R., and Guy, H. R. 1992. Atomic Scale Structure and Functional Models of Voltage-Gated Potassium Channels. *Biophysical Journal* 62: 238-250.

Han, M., Chen, P. Q., and Yang, X. Z. 2005. Molecular dynamics simulation of PAMAM dendrimer in aqueous solution. *Polymer* 46: 3481-3488.

Hancock, R. E., and Diamond, G. 2000. The role of cationic antimicrobial peptides in innate host defences. *Trends in microbiology* 8: 402-410.

Hancock, R. E., and Chapple, D. S. 1999. Peptide antibiotics. *Antimicrob Agents Chemother* 43: 1317-1323.

Henderson, R., Baldwin, J. M., Ceska, T. A., Zemlin, F., Beckmann, E., and Downing, K. H. 1990. Model for the Structure of Bacteriorhodopsin Based on High-Resolution Electron Cryomicroscopy. *Journal of Molecular Biology* 213: 899-929.

Hu, W., Lee, K. C., and Cross, T. A. 1993. Tryptophans In Membrane-Proteins—Indole Ring Orientations And Functional Implications In The Gramicidin Channel. *BIOCHEMISTRY-US* 32: 7035-7047.

Ketchem, R. R., Hu, W., and Cross, T. A. 1993. High-Resolution Conformation Of Gramicidin-A In A Lipid Bilayer By Solid-State Nmr. *Science* 261: 1457-1460.

Killian, J. A., and von Heijne, G. 2000. How proteins adapt to a membrane-water interface. *Trends in Biochemical Sciences* 25: 429-434.

Koeppe, R. E., Killian, J. A., and Greathouse, D. V. 1994. Orientations of the Tryptophan 9 and 11 Side-Chains of the Gramicidin Channel Based on Deuterium Nuclear-Magnetic-Resonance Spectroscopy. *Biophysical Journal* 66: 14-24.

Landoltmarticorena, C., Williams, K. A., Deber, C. M., and Reithmeier, R. A. F. 1993. Nonrandom Distribution of Amino-Acids in the Transmembrane Segments of Human Type-I Single Span Membrane-Proteins. *Journal of Molecular Biology* 229: 602-608.

Lehrer, R. I., and Ganz, T. 1999. Antimicrobial peptides in mammalian and insect host defense. *Curr Opin Immunol* 11: 23-27.

Meers, P. 1990. Location of Tryptophans in Membrane-Bound Annexins. *BIOCHEMISTRY-US* 29: 3325-3330.

Mishra, V. K., Palgunachari, M. N., Segrest, J. P., and Anantharamaiah, G. M. 1994. Interactions of Synthetic Peptide Analogs of the Class a Amphipathic *Helix* with Lipids—Evidence for the Snorkel Hypothesis. *Journal of Biological Chemistry* 269: 7185-7191.

Reithmeier, R. A. F. 1995. Characterization And Modeling Of Membrane-Proteins Using Sequence-Analysis. *Current Opinion In Structural Biology* 5: 491-500.

Ridder, A., Morein, S., Stam, J. G., Kuhn, A., de Kruijff, B., and Killian, J. A. 2000. Analysis of the role of interfacial tryptophan residues in controlling the topology of membrane proteins. *BIOCHEMISTRY-US* 39: 6521-6528.

Schiffer, M., Chang, C. H., and Stevens, F. J. 1992. The Functions Of Tryptophan Residues In Membrane-Proteins. *Protein Engineering* 5: 213-214.

Sieprawska-Lupa, M., Mydel, P., Krawczyk, K., Wojcik, K., Puklo, M., Lupa, B., Suder, P., Silberring, J., Silberring, J., Reed, M., et al. 2004. Degradation of human antimicrobial peptide LL-37 by *Staphylococcus aureus*-derived proteinases. *Antimicrobial Agents and Chemotherapy* 48: 4673-4679.

Strandberg, E., and Killian, J. A. 2003. Snorkeling of lysine side chains in transmembrane helices: how easy can it get? *Febs Letters* 544: 69-73.

Torchilin, V., and Weissig, V. 2003. Liposomes: A Practical Approach; second edition.Oxford University Press, London, UK.

van't H of, W., Veerman, E. C. I., Helmerhorst, E. J., and Amerongen, A. V. N. 2001. Antimicrobial peptides: Properties and applicability. *Biological Chemistry* 382: 597-619.

Vonheijne, G. 1992. Membrane-Protein Structure Prediction—Hydrophobicity Analysis and the Positive-inside Rule. *Journal of Molecular Biology* 225: 487-494.

Vonheijne, G. 1994. Membrane-Proteins—from Sequence to Structure. *Annual Review of Biophysics and Biomolecular Structure* 23: 167-192.

Wimley, W. C., and White, S. H. 1996. Experimentally determined hydrophobicity scale for proteins at membrane interfaces. *Nature Structural Biology* 3: 842-848.

From the foregoing description, various modifications and changes in the compositions and methods of this invention will occur to those skilled in the art. All such modifications coming within the scope of the appended claims are intended to be included therein.

It is further understood that all base sizes or amino acid sizes, and all molecular weight or molecular mass values, given for nucleic acids or polypeptides are approximate, and are provided for description.

All publications, including but not limited to patents and patent applications, cited in this specification are herein incorporated by reference as if each individual publication were specifically and individually indicated to be incorporated by reference herein as though fully set forth.

What is claimed is:

1. An antimicrobial peptide according to formula I:

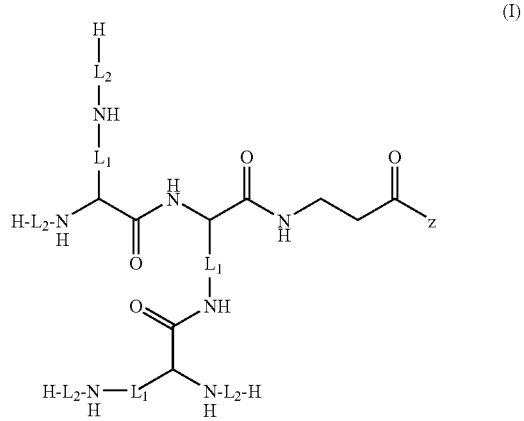

wherein each $L_1$ is —$(CH_2)_n$—; n is 2, 3, 4 or 5; each $L_2$ is WR; wherein WR is -TRP-ARG-, or

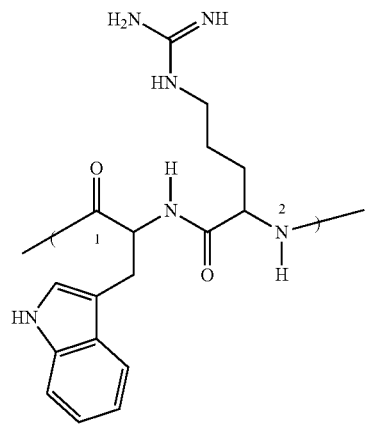

and wherein the C(1) of C(O) is attached to NH and N(2) of NH is attached to H;

and Z is selected from substituted or unsubstituted amino, hydroxy, substituted or unsubstituted alkoxy, and substituted or unsubstituted aryloxy; or a pharmaceutically acceptable salt thereof.

2. The peptide of claim 1, wherein each $L_1$ is selected from —$CH_2$—$CH_2$—, —$CH_2$—$CH_2$—$CH_2$—, and —$CH_2$—$CH_2$—$CH_2$—$CH_2$—.

3. The peptide of claim 1, wherein each $L_1$ is —$CH_2$—$CH_2$—$CH_2$—$CH_2$—.

4. The peptide of claim 1, wherein each Z is selected from $NH_2$, OH, substituted or unsubstituted alkylamino, substituted or unsubstituted arylamino, substituted or unsubstituted alkoxy, and substituted or unsubstituted aryloxy.

5. The peptide of claim 1, wherein each Z is selected from $NH_2$, alkylamino, arylamino, alkoxy and aryloxy.

6. The peptide of claim 1, wherein each Z is selected from nonylamino, benzyl amino, and benzoxy.

7. A peptide according to claim 1, wherein the peptide is according to formula II:

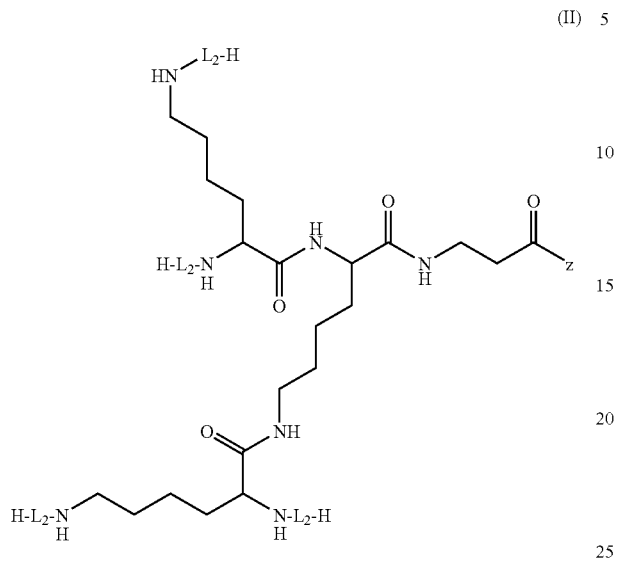

and wherein each $L_2$ is WR; wherein WR is -TRP-ARG-, or

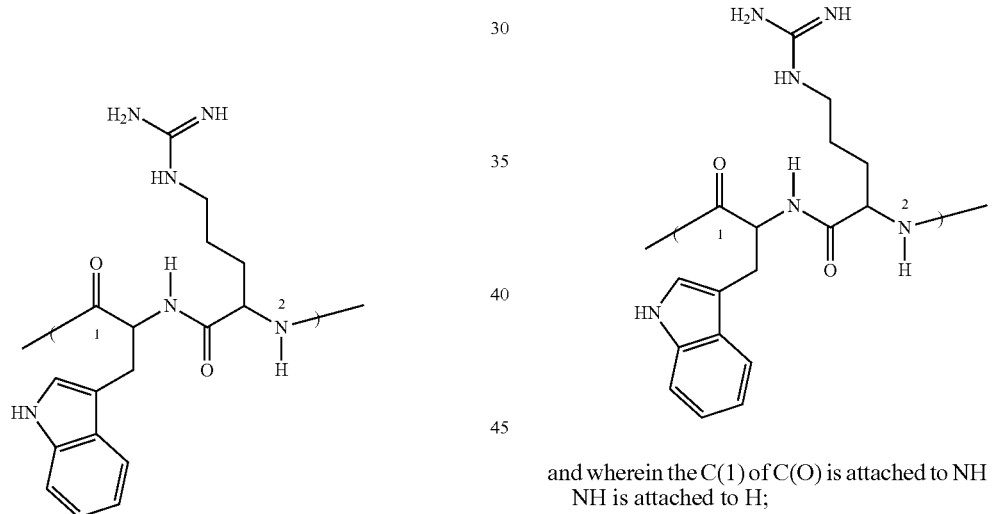

and wherein the C(1) of C(O) is attached to NH and N(2) of NH is attached to H;
and Z is as in claim 1.

8. The peptide of claim 7, wherein each Z is selected from $NH_2$, OH, substituted or unsubstituted alkylamino, substituted or unsubstituted arylamino, substituted or unsubstituted alkoxy, and substituted or unsubstituted aryloxy.

9. The peptide of claim 7, wherein each Z is selected from $NH_2$, alkylamino, arylamino, alkoxy and aryloxy.

10. The peptide of claim 7, wherein each Z is selected from $NH_2$, nonylamino, benzylamino, and benzyloxy.

11. A peptide according to claim 1, wherein the peptide is according to formula III:

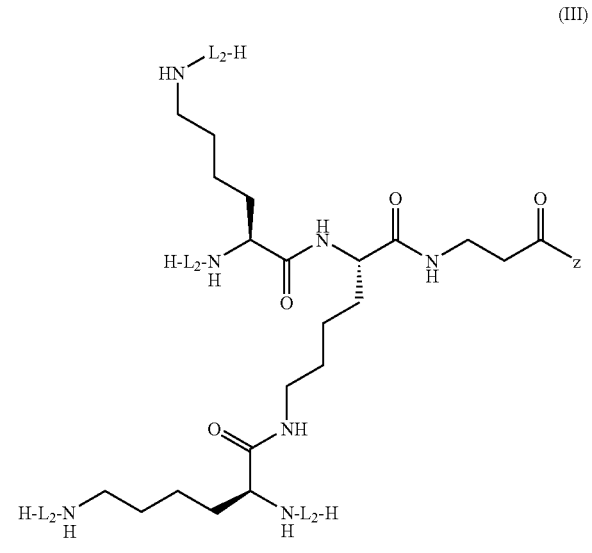

and wherein each $L_2$ is WR; wherein WR is -TRP-ARG-, or and wherein the C(1) of C(O) is attached to NH and N(2) of NH is attached to H;
and Z is as in claim 1.

12. The peptide of claim 11, wherein each Z is selected from $NH_2$, OH, substituted or unsubstituted alkylamino, substituted or unsubstituted arylamino, substituted or unsubstituted alkoxy, and substituted or unsubstituted aryloxy.

13. The peptide of claim 11, wherein each Z is selected from $NH_2$, alkylamino, arylamino, alkoxy and aryloxy.

14. The peptide of claim 11, wherein each Z is selected from $NH_2$, nonylamino, benzylamino, and benzyloxy.

15. A pharmaceutical composition comprising a pharmaceutically acceptable carrier and a pharmaceutically effective amount of the peptide of claim 1.

16. The pharmaceutical composition of claim 15, wherein the carrier is a parenteral carrier, oral or topical carrier.

17. A therapeutic composition comprising a peptide of claim 1, prepared as a hydrogel.

* * * * *